(12) United States Patent
Fila et al.

(10) Patent No.: US 8,348,034 B2
(45) Date of Patent: Jan. 8, 2013

(54) CAUTERIZING SYSTEM

(75) Inventors: Ryan Fila, Wenatchee, WA (US); John Scott Berglin, Wenatchee, WA (US)

(73) Assignee: Ryan Fila, Wenatchee, WA (US)

( * ) Notice: Subject to any disclaimer, the term of this patent is extended or adjusted under 35 U.S.C. 154(b) by 697 days.

(21) Appl. No.: 12/419,206

(22) Filed: Apr. 6, 2009

(65) Prior Publication Data

US 2009/0287211 A1    Nov. 19, 2009

Related U.S. Application Data

(63) Continuation-in-part of application No. PCT/US2007/080631, filed on Oct. 5, 2007.

(60) Provisional application No. 60/850,062, filed on Oct. 6, 2006.

(51) Int. Cl.
*H02G 11/02* (2006.01)
*B21C 47/00* (2006.01)

(52) U.S. Cl. .................. 191/12.2 R; 242/360

(58) Field of Classification Search ............. 191/12 R, 191/12.2 R, 12.4; 242/360, 362, 364, 370, 242/371, 382
See application file for complete search history.

(56) References Cited

U.S. PATENT DOCUMENTS

| | | | |
|---|---|---|---|
| 2,710,610 A | 6/1955 | Woodruff | |
| 3,705,962 A * | 12/1972 | Banister | 191/12.4 |
| 4,674,498 A | 6/1987 | Stasz | |
| 6,210,329 B1 | 4/2001 | Christmas et al. | |
| 6,327,507 B1 | 12/2001 | Buchan | |
| 6,803,525 B1 * | 10/2004 | Liao | 174/135 |
| 6,871,812 B1 * | 3/2005 | Chang | 242/378.1 |
| 2004/0149533 A1 * | 8/2004 | Milano | 191/12.4 |

OTHER PUBLICATIONS

PCT International Search Report and Written Opinion from counterpart PCT Application No. PCT/US2007/080631, mailed on May 19, 2008, 10 pages.

* cited by examiner

*Primary Examiner* — Robert McCarry, Jr.
(74) *Attorney, Agent, or Firm* — Seed IP Law Group PLLC

(57) ABSTRACT

A cauterizing system having a cauterizer tool for performing cauterization procedures, a cauterizer cord for carrying power to the cauterizer tool, a plug and a power cord for carrying power from the plug to the cauterizer cord, and a housing in which is mounted a mechanism for retracting and extending the cauterizer cord and the power cord.

14 Claims, 22 Drawing Sheets

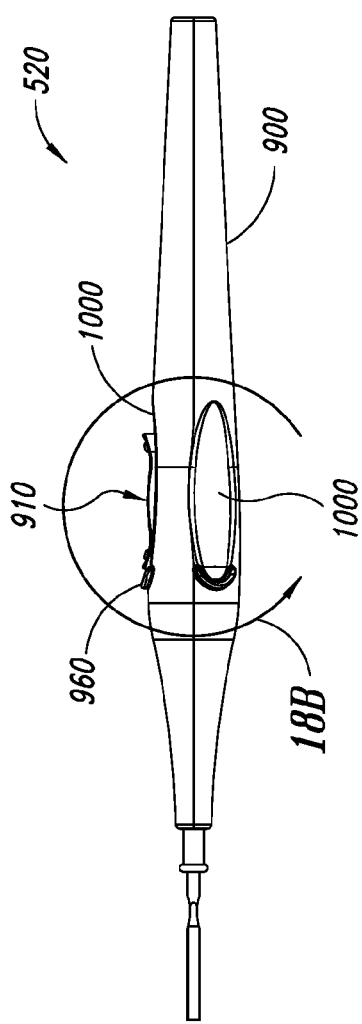
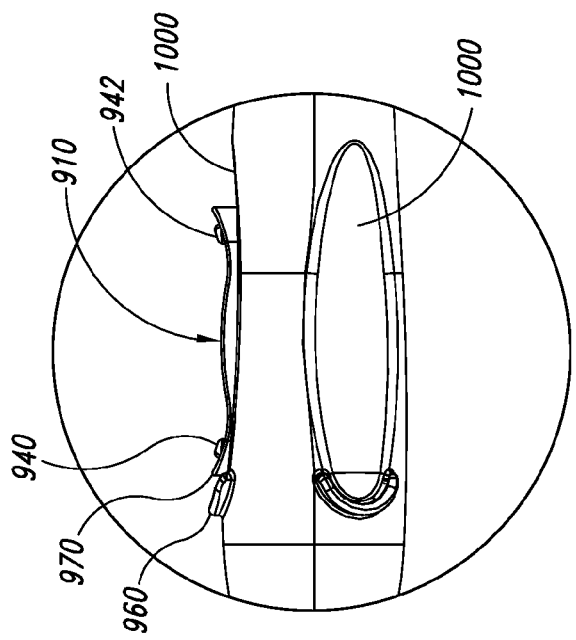
FIG. 18A
FIG. 18B

CAUTERIZING SYSTEM

CROSS-REFERENCE TO RELATED APPLICATIONS

This application is a continuation-in-part application of International Application No. PCT/US2007/080631, filed on Oct. 5, 2007, which claims priority under 35 U.S.C. §119(e) of U.S. Provisional Patent Application No. 60/850,062 filed Oct. 6, 2006. These two applications are incorporated herein by reference in their entireties.

BACKGROUND

1. Field

The present disclosure generally relates to medical systems and methods for using the same and, more particularly, to cauterizing systems with one or more deployable cords.

2. Background Discussion

Electrocautery units (ECU) are used in surgery to cauterize tissue in order to control bleeding. A packaged ECU often includes a cautery pencil and a bound up cautery cord extending from the cautery pencil to a plug. Typically, the cautery cord is folded up (e.g., in an accordion type style) such that the cord has an unwanted folded configuration (i.e., a shape memory configuration) when the ECU is removed from its packaging. This makes it difficult to maneuver the ECU around surgical sites.

Clamps are used to mount the ECU on a sterile support in a sterile environment. Traditional clamps are cumbersome and difficult to use. After the ECU is mounted on a sterile field with the clamps, the cautery pencil is used to cauterize tissue. It may be difficult to comfortably maneuver cautery pencils throughout a long procedure because cautery pencils are often somewhat bulky and uncomfortable to hold. Cautery cords are not long enough to permit convenient maneuvering of the cautery pencil about many surgical sites. If there are multiple working surgical sites, for example, there may be an appreciable risk of pulling the ECU off of the sterile field, thereby disrupting the surgical procedure.

Because cautery pencils are connected to cords that are not readily visually distinguishable from the surrounding environment, difficulties can arise in avoiding interference with the cord. For example, if the cautery cord is blue, the cord may visually blend with blue surgical drapes that are often used in surgical rooms. Additionally, the cautery cord may have a similar appearance to other cords in proximity to the surgical sites and may cause confusion during a surgical procedure. Thus, it may be difficult to keep track of the cord during a surgical procedure or to see and avoid unwanted contact, pulling, tripping over, and the like.

BRIEF SUMMARY

Some embodiments disclosed herein provide a system with a flexible cord without an appreciable amount of memory that facilitates rapid set-up to decrease the overall surgical time. Reducing the surgical time may reduce risks associated with performing surgery. The system can be mounted on a surface or structure without using complicated clamps, thus enabling physicians, nurses, technicians, and other users to easily mount the system on various types of mounting surfaces or structures.

Representative embodiments disclosed herein are generally directed towards cauterizing systems and methods of using the same. In particular, a cauterizing system includes a cauterizer handpiece, a main housing, and a deployable handpiece cord extending between the cauterizer handpiece and the main housing. In some aspects, the handpiece cord is an extendable and retractable cord. The extendable and retractable cord can be easily kept away from the surgical site.

In some embodiments, a cauterizing system is provided that includes a housing, a cauterizer tool, a cauterizer cord for carrying power between the housing and the cauterizer tool, a plug, and a power cord for carrying power between the plug and the housing. In some aspects, the cauterizer cord is extendable and retractable relative to the housing. In some aspects, the power cord is extendable and retractable relative to the housing. In some aspects, a retraction mechanism is positioned on or in the housing. The retraction mechanism is configured to provide extending and retracting of the cauterizer cord. In some other aspects, the retraction mechanism is configured to provide extending and retracting of the power cord. In some aspects, the cauterizing system includes an apparatus for mounting the housing on a support surface, such as, without limitation, an adhesive member or a hook and loop fastener assembly. In some aspects, the retraction mechanism delivers energy from the power cord to the cauterizer cord. A conductive biasing member of the retraction mechanism connects the power cord to the cauterizer cord. Electrical energy is delivered from the power cord to the cauterizer cord via the conductive biasing member, while the conductive biasing member allows the cauterizer cord to be pulled from the housing.

In some embodiments, an electrosurgical unit (ESU) has a handpiece, a main housing, and an extendable and retractable cord extending between a power plug and the main housing. The main housing can be a handheld housing for convenient transport.

In yet other embodiments, a cauterizing system is provided that includes a main body, a cauterizer handpiece, a plug, and first and second extendable and retractable cords coupling (either directly or indirectly) the cauterizer handpiece and plug, respectively, to the main body. In some aspects, an actuation mechanism disposed in the main body selectively pulls the first cord or second cord or both into the main body.

The cauterizing system can be an electrocautery unit suitable for use in a wide range of procedures. The size, shape, and configuration of the cauterizing system can be selected based on the desired range of motion of the cautery handpiece.

In some embodiments, a cauterizing system includes a cauterizer handpiece, a cauterizer cord, a portable cord dispenser, and an adhesive member. The cauterizer handpiece is adapted to cauterize tissue. The cauterizer handpiece includes an elongate main body dimensioned and configured to be manually gripped by a user. A cautery tip extends from the elongate main body. A manually operable input device is positioned along the elongate main body and spaced from the cautery tip. A stop adjacent the input device is configured to position at least a portion of the user's hand relative to the input device. The input device is adapted to control a temperature of the cautery tip. The cauterizer cord is adapted to carry power to the cauterizer handpiece. The portable cord dispenser has a chamber, a cord actuation device in the chamber, and a holder dimensioned to releasably hold the cauterizer handpiece. The cauterizer cord is coupled to the cord actuation device such that the cauterizer cord is extendable and retractable relative to the cord dispenser. The power cord is adapted to carry power to the cord dispenser. The adhesive member is fixedly coupled to the cord dispenser. The adhesive member has a bonding surface adapted to be attached to a mounting surface such that the cord dispenser remains attached to the mounting surface while the cauterizer cord is extended from the cord dispenser.

In some embodiments, a cauterizing system includes a cauterizer tool adapted to cauterize tissue, a cauterizer cord adapted to carry power to the cauterizer tool, and a portable cord dispenser having a chamber and a cord actuation device in the chamber. The cauterizer cord is coupled to the actuation device such that the cauterizer cord is extendable and retractable relative to the cord dispenser. In some embodiments, the power cord is adapted to carry power to the cord dispenser. A plug can be coupled to the power cord. The plug is adapted to engage a power supply.

In some embodiments, a method of using a cauterizing system is provided. The method includes attaching a cord dispenser to a support surface. A cauterizer handpiece is moved relative to the cord dispenser attached to the support surface so as to extend a cauterizer cord from the cord dispenser. The cauterizer handpiece is applied to a target location. Power is applied to the cauterizer handpiece via the cauterizer cord.

In some embodiments, a cauterizer handpiece includes a main body dimensioned and configured to be manually gripped by user, a cautery tip extending from the main body, and a manually operable input device positioned along the main body and spaced from the cautery tip. The input device is adapted to control a temperature of the cauterizy tip. The cauterizer handpiece can further include a locator adjacent the input device for positioning at least a portion of a user's hand relative to the input device.

In yet other embodiments, a cord dispenser includes a cord guide through which a first cord extends. The cord guide is rotatably coupled to a main body, which surrounds a cord retraction mechanism, so as to position the first cord with respect to a second cord. The retraction mechanism can retract the first cord or second cord, or both.

In some other embodiments, a multi-cord device is used in medical environments in which sterile conditions are desired to enhance patient safety, for example, during surgeries. In certain embodiments, the multi-cord device provides a medical surgeon with a sufficient length of sterile cord to service an instrument, while at the same time providing a barrier to contamination from a power cord of the device which contacts a non-sterile environment (e.g., the floor, shoes, counters, waste baskets, etc). At least some embodiments disclosed herein can have a relatively low manufacturing cost and are therefore disposable. The multi-cord device can be incorporated into an ESU or other type of device to provide a desired electrical current profile. Conventional medical equipment with swiveling electrical components often have impaired electrical current profiles (e.g., frequency, voltage, and amperage) due to current compromising impedance of traditional armature assemblies (e.g., brush type armature assemblies) or slip-ring technologies often used to transfer power through swiveling joints. Embodiments disclosed herein are configured to maintain a desired current profile as the multi-cord device is moved between different configurations.

A sterile spring-loaded electrical cord retraction device, in some embodiments, includes a retraction device with one or more of retracting springs that serve a dual purpose of providing communication, for example, conducting electrical current or transmitting electrical signals or data through a single or multiple wires in a cord without compromising (e.g., breaking) the circuit(s) or compromising current or signal quality. In certain embodiments, a cord is capable of being wound about a free-moving spindle assembly, such that one end of the cord may be pulled out for use, while the other end of the cord remains anchored to the spindle assembly. A retraction spring in the form of a coiled spring is anchored to the spindle assembly at one end and fixed to a component inside of a sterile housing. The coiled spring is capable of transmitting an electrical current to a fixed end of the spring electrically coupled to a service cord that supplies current from outside (e.g., a non-sterile side) of the device. The end of the spring is electrically coupled to a spool-end of the wound cord. A continuous current from the spring can be supplied through the sterile cord as the sterile cord is extended or retracted. The retraction device may be used to transmit exceptionally high frequencies to conduct extreme volt-amp related currents suitable for electrocautery and other medical procedures in an operating room environment. The cord retraction device can have any number of independent circuits to independently deliver current through the device.

BRIEF DESCRIPTION OF THE SEVERAL VIEWS OF THE DRAWINGS

The foregoing and other features and advantages of the disclosed embodiments will be more readily appreciated as the same become better understood from the following detailed description when taken in conjunction with the accompanying drawings, wherein:

FIG. 18A is a side elevational view of a cauterizer handpiece;

FIG. 18B is a detailed view of the cauterizer handpiece taken along 18B of FIG. 18A;

DETAILED DESCRIPTION

The following detailed description is generally directed towards medical systems and methods of using the same. Many specific details of certain embodiments of the present disclosure are set forth in the following description and in FIGS. 1-28 to provide a thorough understanding of such embodiments. One skilled in the art, however, will understand that the disclosed embodiments may have additional features or may be practiced without one or more of the details presented in the following description.

Figure 1:
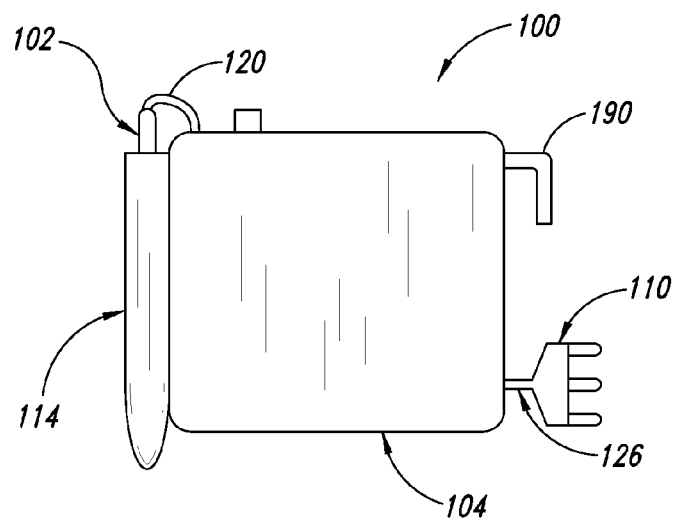
FIG. 1 is an elevational view of a cauterizing system.
Figure 2:
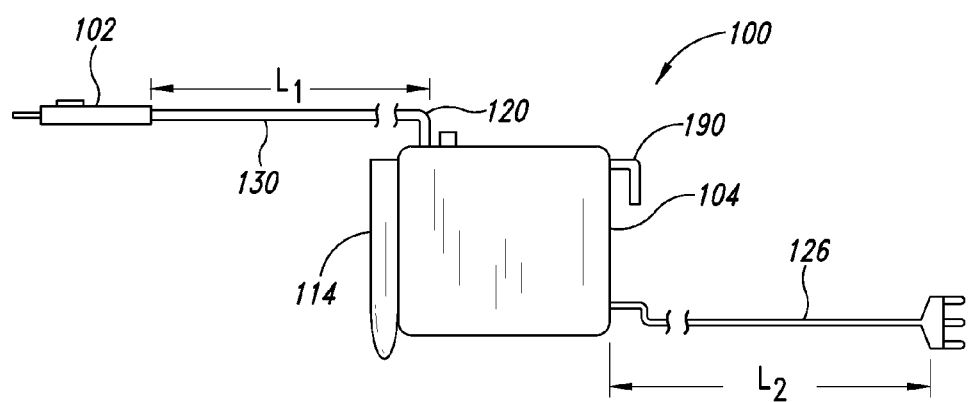
FIG. 2 is an elevational view of the cauterizing system of FIG. 1, where a cauterizer handpiece and plug are extended from a housing of the cauterizing system.

FIGS. 1 and 2 illustrate a cauterizing system 100 that includes a cauterizer handpiece 102 and a handpiece cord 120 coupling the handpiece 102 to a power source (not shown) and to a cord dispenser 104. The illustrated cauterizer handpiece 102 of FIG. 1 is retained in a holder 114, which is permanently or temporarily coupled to the cord dispenser 104. As shown in FIGS. 1 and 2, the handpiece cord 120 is stored in the cord dispenser 104 and extends between the cauterizer handpiece 102 and cord dispenser 104. A power cord 126, stored in the cord dispenser 104, extends between the cord dispenser 104 and a plug 110. When the plug 110 is plugged into the power source, electrical energy can be delivered to the cauterizer handpiece 102 via the handpiece cord 120 and power cord 126. The activated handpiece 102 can be used to cauterize, burn, or otherwise treat a cauterizing location, such as tissue, during surgery and after a surgical procedure.

One or both of the cords 120, 126 are extendable or retractable or both in order to regulate their lengths. The cords 120, 126 can be flexible cords without any appreciable preset configuration when dispensed from the cord dispenser 104, thereby facilitating set-up to reduce overall surgical time. The illustrated cords 120, 126 are independently movable between a retracted position (FIG. 1) and an extended position (FIG. 2). This enables use of the system 100 in various types of settings. The system 100 is adapted for use in a wide range of settings, including, without limitation, hospitals, emergency rooms, operating rooms, medical transport vehicles (e.g., ambulances), on battlefields, and other settings in which a patient may need cauterizing, such as to stop unwanted bleeding.

When the cauterizer handpiece 102 is removed from the holder 114 (illustrated as a sheath-type holder), the cord 120 can be pulled out of the cord dispenser 104. A majority of the cauterizer cord 126 can be stored in the cord dispenser 104 when the cauterizer handpiece 102 is held by the holder 114. In such embodiments, the cauterizing system 100 can be conveniently carried without interference from the cauterizer cord 126. In some embodiments, at least 70%, 80% or 90%, or ranges encompassing such percentages, of the overall length of the cord 126 is stored in the cord dispenser 104.

As shown in FIG. 2, the handpiece cord 120 has an overall length $L_1$, (i.e., the length of the section of the cord 120 extending between the cauterizer handpiece 102 and the cord dispenser 104). The length $L_1$ can be selected to permit the cord dispenser 104 to be mounted on a suitable support structure while the handpiece 102 is in use. The cord dispenser 104 can be mounted on a bed (e.g., a bedrail or frame), drape, clothing, stationary or movable medical tower, mayo stand, medical instrument (e.g., patient monitoring equipment), or other suitable mounting structures or surfaces typically found in proximity to a surgical field or to a patient undergoing a cauterization procedure. The length $L_1$ of the handpiece cord 120 is sufficiently long to permit use of the cauterizer handpiece 102 when the cord dispenser 104 remains coupled to any one of these mounting areas.

The illustrated handpiece cord 120 is a flexible electrical cord, preferably without any appreciable preset configuration, such as a coiled configuration. Traditional cauterizers often have cords that are folded-up and stored, thus imparting a preset shape to the cords. Unlike these traditional cauterizers, a section 130 of the disclosed handpiece cord 120 pulled from the cord dispenser 104 can be easily bent, twisted, folded, straightened, or otherwise manipulated. Because the flexible cord section 130 can be easily manipulated, it can be kept out of the way of the surgeon during a surgical procedure. In some embodiments, the cords have substantially no memory such that the cords can be moved without disrupting the surgical field.

In some embodiments, the cords 120, 126 are colored or otherwise visually distinct from the surrounding environment. If the cords 120, 126 are in proximity to drapes, the color of the cords 120, 126 can be visually distinct from the drapes. For example, if drapes near the surgical site are blue, the cords 120, 126 can be different color (e.g., white, red, and the like) to increase the visibility of the cords 120, 126 as compared to cords that blend with the surrounding environment. In this manner, unwanted contact with the cords 120, 126 can be avoided. The cords 120, 126 can be different colors to indicate different environments. A user can determine which cord 120, 126 should be in a particular environment (e.g., sterile or non-sterile environment) based on the cord colors. During a procedure, the cords 120, 126 can be conveniently kept in certain areas based on their color. For example, the cord 120 may be white to indicate that the cord 120 should be kept in a sterile environment. The cord 126 may be red to indicate that it can be kept in a non-sterile environment.

Generally, the maximum length $L_1$ of the handpiece cord 120 can be at least about 10 feet, 8 feet, 7 feet, 6 feet, 5 feet, 4 feet, or 3 feet, or in ranges encompassing such lengths. In some embodiments, for example, the handpiece cord 120 has a length $L_1$ of about 4 feet to provide sufficient slack to perform procedures typically performed with the cauterizer handpiece 102. The cord dispenser 104 can remain stationary throughout a portion of the cauterizing procedure or the entire cauterizing procedure. Advantageously, the cord dispenser 104 can be repositioned during the surgical procedure, if needed or desired. For example, the cord dispenser 104 can be mounted on a first support structure to perform a first cauterization procedure and then mounted on a second support structure to perform a second cauterization procedure. The cord dispenser 104 can be manually repositioned any number of times, thus allowing the cauterizing system 100 to be used in a wide range of procedures.

Similarly, the flexible power cord 126 of FIG. 2 can also be easily manipulated. In some embodiments, a maximum length $L_2$ of the power cord 126 can be about 12 feet, 8 feet, 7 feet, 6 feet, 5 feet, or 4 feet, or in ranges encompassing such lengths. When the plug 110 is connected to a power outlet (such as an AC power outlet), electrical energy from the plug 110 powers the cauterizer handpiece 102 through appropriate control and regulator circuitry. The cords 120, 126 can be discontinuous or continuous monopolar cords, bipolar cords, or other type of conduits or insulated cables for providing electrical power. Various types of components (e.g., adapters, connectors, or other electrical components) can be positioned along one or both of the cords 120, 126.

In some embodiments, the plug is a connector for engaging a connector of a power outlet in the form of a battery or power cell. The plug 110 can be a type A plug, type B plug, or any other type of known plug for connecting to a power outlet. Such plugs are readily commercially available and will not be described in detail herein.

Figure 3:
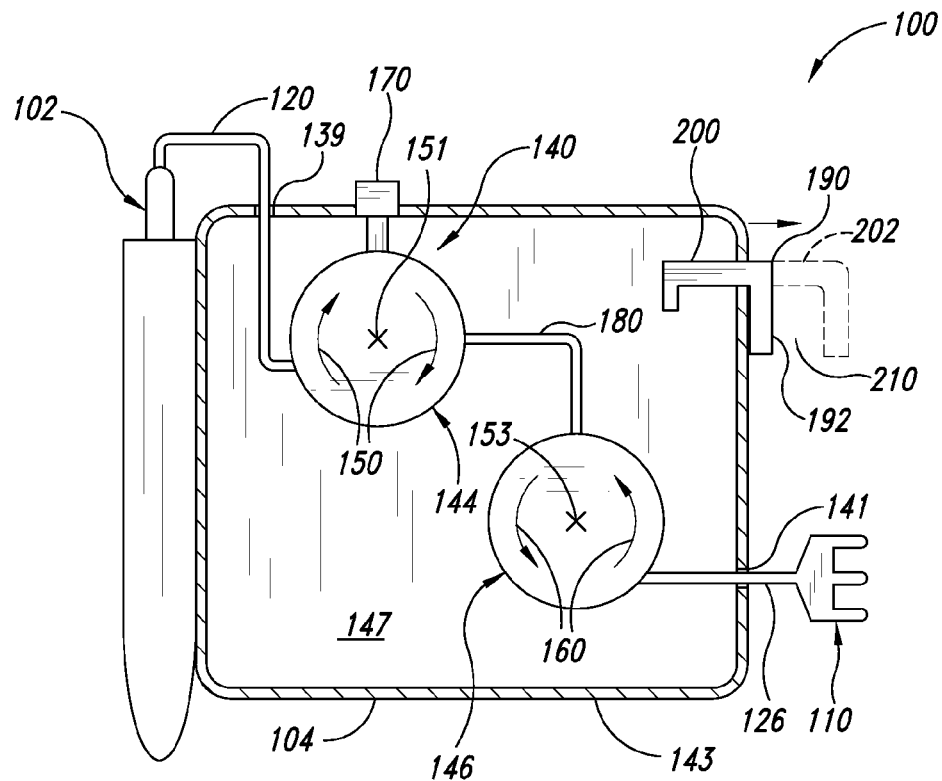
FIG. 3 is a partial cross-sectional view of the cauterizing system of FIG. 1.

FIG. 3 illustrates a cord actuation device 140 in the form of a retracting mechanism for automatically retracting one or both of the two cords 120, 126. The retracting mechanism 140 has a first spindle assembly 144 and a second spindle assembly 146. The cords 120, 126 are wound on the first and second spindle assemblies 144, 146, respectively. The cauterizer cord 120 extends between the plug 110 and spindle assembly 144 and passes through an aperture 139 in a housing 143 of the actuation device 140. The power cord 126 extends between the cauterizer handpiece 102 and the spindle assembly 146 and passes through an aperture 141 in the housing 143. The housing 143 defines a chamber 147 for accommodating the cord actuation device 140.

When the cauterizer handpiece 102 is pulled away from the cord dispenser 104, the first spindle assembly 144 is rotated clockwise (indicated by the arrows 150) by the handpiece cord 120. When the plug 110 is pulled away from the cord dispenser 104, the spindle assembly 146 is rotated counter-clockwise (indicated by the arrows 160) by the power cord 126. The spindle assemblies 144, 146 are thus independently rotatable about axes of rotation 151, 153, respectively.

One or both of the spindle assemblies 144, 146 can be biased to tension one or both of the cords 120, 126. One or more biasing members, torquing systems, or other suitable force generation devices known to those skilled in the art can be used to pull the cords 120, 126 into the cord dispenser 104 with a desired force. A biasing member can include, but is not limited to, one or more springs (e.g., helical springs, coil springs, torsion springs, and the like) or other type of device adapted to apply forces suitable for retracting an extended cord.

A control element 170 shown in FIG. 3 can be used to change the operating state of the retracting mechanism 140. For example, the control element 170 can selectively lock and unlock one or both of the spindle assemblies 144, 146 in the retracting mechanism 140. Once one or both of the cords 120, 126 are extended (partially or fully extended) out of the cord dispenser 104, the control element 170 can lock one or both of the spindle assemblies 144, 146. To adjust the lengths $L_1$, $L_2$ of the cords 120, 126, the control element 170 can unlock the spindle assemblies 144, 146. In some embodiments, once the cord 126 is deployed, the spindle assembly 146 self-locks and prevents retracting of the cord 126. As shown in FIG. 3, the control element 170 can unlock the spindle assembly 144 such that the spindle assembly 144 retracts the cord 120. Various types of self-locking mechanisms, such as ratcheting mechanism, can be incorporated into the cord dispenser 104.

A connector cord 180 extends between the spindle assemblies 144, 146 and provides electrical communication between the cords 120, 126. One of ordinary skill in the art can select the type and configuration of the connector cord 180 based on the design of the retracting mechanism 140. In some embodiments, a single cord can form both cords 120, 126. For example, a continuous and uninterrupted cord can be used to form the cord segments 120, 126, 180 illustrated in FIG. 3.

The cauterizer handpiece 102 can be sized to fit comfortably in a user's hand. In some embodiments, the cauterizer handpiece 102 is somewhat similar in shape and size to a typical pen used for writing. Thus, the cauterizer handpiece 102 can be more slender than traditional wide body cauterizers. In some embodiments, the cauterizer handpiece 102 can have interchangeable disposable cautery tips. In other embodiments, the cauterizer handpiece 102 has a permanent cautery tip. Based on the procedures to be performed, one of ordinary skill in the art can select an appropriate cautery tip.

The cauterizer handpiece 102 can have one or more gripping features for facilitating proper finger placement. The gripping features can be contoured surfaces, grooves, protrusions, or other features configured and positioned to provide a comfortable grip and to improve control and maneuverability of the cauterizer handpiece 102. Contoured gripping features are discussed in connection with FIGS. 6-18A.

Various types of handpieces or instruments can be used with the system 100. For example, the handpiece can be a cauterizing tool, cautery pencil, surgical cutting tool (e.g., a rotary or linear cutting handpiece), optical device (e.g., endoscope), camera, transducer, diagnostic equipment, or other electrical device used in the medical field.

The cord dispenser 104 of FIG. 3 has a mounting system 190 for mounting the cord dispenser 104 on various types of structures, such as, for example, rods, rails, hooks, arms, medical towers, mobile portable stands, peel-away adhesives, pressure clips, twist clamps, and the like. The cord dispenser 104 can have a relatively large flat area suitable to which one or more mounting systems can be positioned. The illustrated mounting system 190 has an angled elongate arm 192 slidably coupled to the cord dispenser 104. The angled arm 192 is movable between an initial position 200 and an extended position 202 (shown in phantom). The cord dispenser 104 and elongate arm 192 define a window 210 sized to be received over a structure to which the system 100 can be mounted. Alternatively, the cord dispenser 104 can be anchored to a wide range of different types of surfaces using adhesives that can withstand forces imparted by repeatedly extending and retracting the cords. After use, the user can conveniently detach the cord dispenser 104 from the anchoring surface.

The cauterizing system 100 and its components can be disposable or non-disposable. As used herein, the term "disposable" when applied to a system or component (or combination of components), such as a cauterizer handpiece or cauterizing system, is a broad term and generally means, without limitation, that the system or component in question is used a finite number of times and then discarded. Some disposable components, such as a disposable cautery tip (including a heating element), are used only once and then discarded. In some embodiments, the entire cauterizing system 100 is disposable.

The cauterizing system 100 can be portable for convenient transport to the desired mounting area. The illustrated cauterizing system 100 is dimensioned to be manually carried and positioned to reduce setup time.

If the handpiece 102 and cord dispenser 104 are located in a sterile environment, the deployed cord 126 may extend through a non-sterile environment. The spindle assembly 146 may prevent retracting of the power cord 126, which may be contaminated, to maintain the sterility of the sterile environment.

Figure 4:
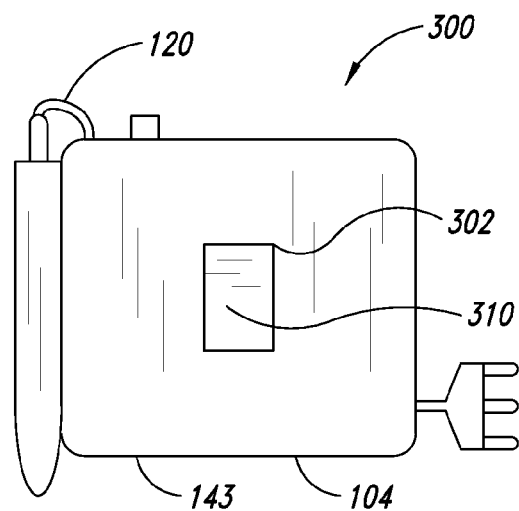
FIG. 4 is an elevational view of a cauterizing system, in accordance with another illustrated embodiment.

FIG. 4 illustrates a cauterizing system 300 that is generally similar to the cauterizing system of FIGS. 1-3, except as detailed below. Where possible, identical or similar components, elements, or structures of the embodiment of FIGS. 1-3 are used in FIG. 4.

The cauterizing system 300 of FIG. 4 has a mounting system 302 in the form of an adhesive member. The adhesive member can have a bonding surface 310 suitable for placement on various types of mounting surfaces. The mounting system 302 can be used to temporarily or permanently couple the cauterizing system 300 to fabric (e.g., a patient's gown, drapes, physician's clothing), or the surfaces of other devices or instruments as disclosed herein. In some embodiments, once a procedure is completed, the system 300 can be detached from a mounting surface and discarded or reused.

The adhesive member 302 of FIG. 4 may be fixedly coupled to the cord dispenser 104. Adhesion between the adhesive member 302 and the mounting surface may keep the cord dispenser 104 coupled to the mounting surface when the handpiece cord 120 is dispensed, even when the user has to overcome a biasing force to dispense the cord 120. The cord dispenser 104 can thus remain coupled to the mounting surface while one or both of the cords 120, 126 are dispensed.

As used herein, the term "adhesive member" includes, without limitation, one or more adhesive sheets, glues, bonding agents, or other materials or components suitable for coupling to a mounting surface. In some embodiments, the adhesive member is an adhesive sheet (either flexible or rigid) coupled (e.g., or bonded) adhered to an outer surface of the housing 143. In some embodiments, a bonding agent sandwiched between the chord dispenser 104 and the mounting surface forms the adhesive member.

Figure 5:
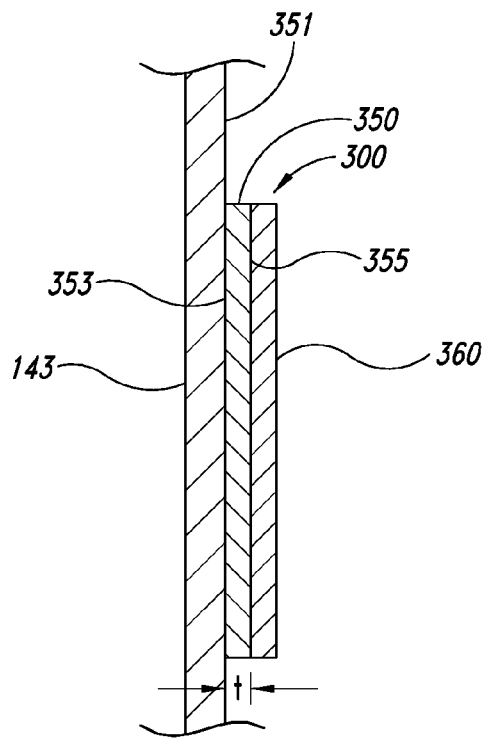
FIG. 5 is an elevational cross-sectional view of a mounting system of a cauterizing system.
Figure 6:
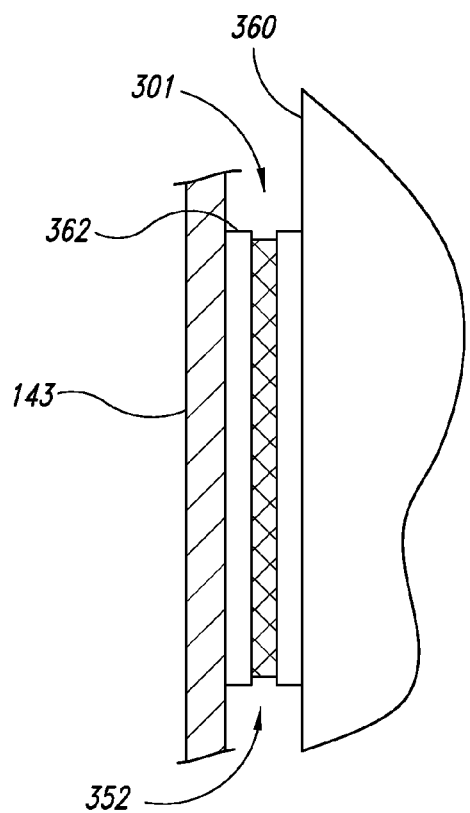
FIG. 6 is a side elevational view of a mounting system of a cauterizing system, in accordance with another illustrated embodiment.

FIGS. 5 and 6 illustrate multi-piece mounting systems 300, 301. The mounting system of FIG. 5 includes an adhesive member 350 fixedly attached between an outer surface 351 of the housing 143 and a release liner 360. First and second surfaces 353, 355 of the adhesive member 350 define a thickness t. The thickness t can be increased or decreased to increase or decrease, respectively, the standoff distance of the cauterizing system. The first surface 353 can be permanently coupled to the cord dispenser housing 143, if needed or desired.

The release liner 360 can be separated from the adhesive member 350 to expose an outwardly facing surface formed or coated, in whole or in part, with one or more adhesives (e.g., pressure sensitive adhesives, medical adhesives, bonding agents, and the like). The adhesion strength of the adhesive member 350 applied to a surface may be sufficiently high such that the cord dispenser 104 remains continuously coupled to the surface while the cauterizer cord 120 is moved relative to the cord dispenser housing 143.

In some embodiments, the cord dispenser 104 can be adhesively coupled to a surface using the adhesive member 350. The cauterizer handpiece 102 can be moved relative to the cord dispenser 104, which is coupled to the surface, so as to extend a cauterizer cord 120 from the cord dispenser 104. A user can move the cauterizer handpiece 102 to overcome a biasing force applied by the cord actuation device 140, thus pulling the cauterizer cord 120 out of the cord dispenser 104.

To power the cauterizer handpiece 102, the power cord 126 is dispensed from the cord dispenser 104. The power cord 126 carries power from the plug 110 in a non-sterile environment while the cauterizer cord 120 is in a sterile environment. The cauterizer handpiece 102 can be used in the sterile environment while the power cord 126 provides access to a power supply in the non-sterile environment.

The cauterizer handpiece 102 can be applied to a location to be cauterized (e.g., a surgical site). After performing the procedure, the user can break adhesion between the surface and the adhesive member 350 to separate the cord dispenser 104 from the surface. The cord dispenser 104 can then be adhesively attached to another location.

FIG. 6 shows a mounting system 301 having a hook and loop fastener assembly 352 used to removably attach the cord dispenser housing 143 to a mounting surface 360. A hook sheet 362 of the fastener assembly 352 can be permanently coupled to the cord dispenser 104.

Figure 7:
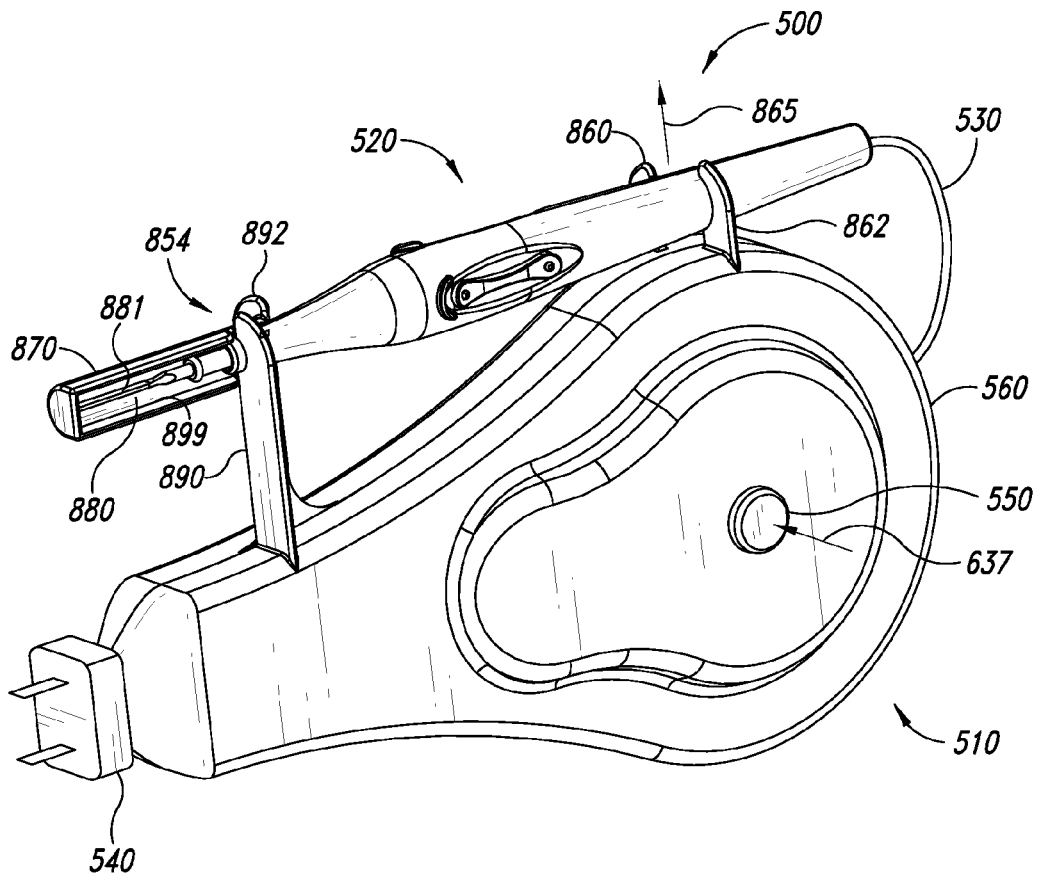
FIG. 7 is an isometric view of a cauterizing system, in accordance with another illustrated embodiment.

FIG. 7 illustrates a cauterizing system 500 in accordance with another embodiment. The cauterizing system 500 includes a cord dispenser 510 and a cauterizer handpiece 520 removably mounted on the cord dispenser 510. A user can quickly and conveniently remove the cauterizer handpiece 520 from the cord dispenser 510. A plug 540 can be easily gripped and pulled away from a tapered end of the cord dispenser 510. The cord dispenser 510 further includes an accessible control element 550 for controlling the length of a handpiece cord 530.

Figure 8:
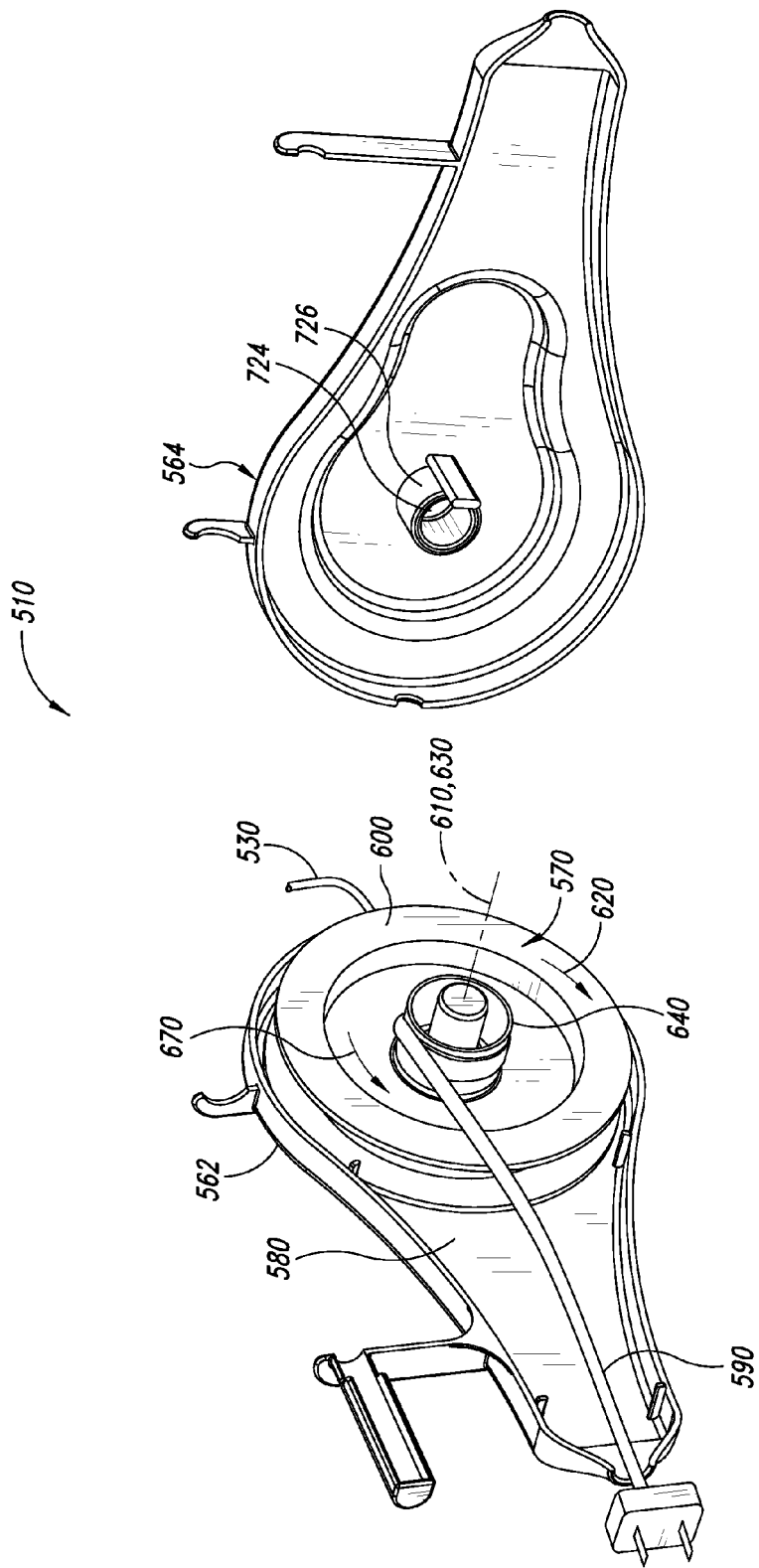
FIG. 8 shows the cauterizing system of FIG. 7, wherein side housings are separated from one another.

Referring to FIGS. 7 and 8, the cord dispenser 510 includes a housing 560 that surrounds a cord actuation device 570. In some embodiments, including the illustrated embodiment of FIG. 8, the housing 560 includes two complementary side housings 562, 564 that define an interior chamber 580 dimensioned to accommodate the cord actuation device 570.

The handpiece cord 530 and the power cord 590 extend outwardly through corresponding apertures at opposite sides of the cord dispenser 510. The cord actuation device 570 is interposed between the outwardly extending sections of the cords 530, 590. To extend the handpiece cord 530, a spindle assembly 600, about which the handpiece cord 530 is wound, can rotate about an axis of rotation 610 (indicated by the arrow 620). Likewise, to extend the power cord 590, the spindle assembly 640 about which the power cord 590 is wound, can rotate about an axis of rotation 630 (indicated by the arrow 670). The axes of rotation 610, 630 can be collinear, parallel, non-parallel, offset from each other (see axes 151, 153 of FIG. 3), or at any other orientation with respect to one another.

The cord actuation device 570 can be a retracting mechanism having a first state for extending the handpiece cord 530 and a second state for retracting the handpiece cord 530. In the first state, the cord actuation device 570 allows a user to pull the handpiece cord 530 out of the housing 560. The cord actuation device 570 can also be self-locking to minimize, limit, or substantially prevent retraction of the partially or fully extended handpiece cord 530. In the second state, the cord actuation device 570 is configured to retract the partially or fully extended handpiece cord 530.

The control element 550 of FIG. 7 is movable between a first position and a second position corresponding to the cord actuation device 570 in the first and second states, respectively. The first position can be a raised position, and the second position can be a depressed position. For example, the control element 550 in the raised starting position can be moved inwardly (indicated by the arrow 637 of FIG. 7) to the depressed position.

Figure 9:
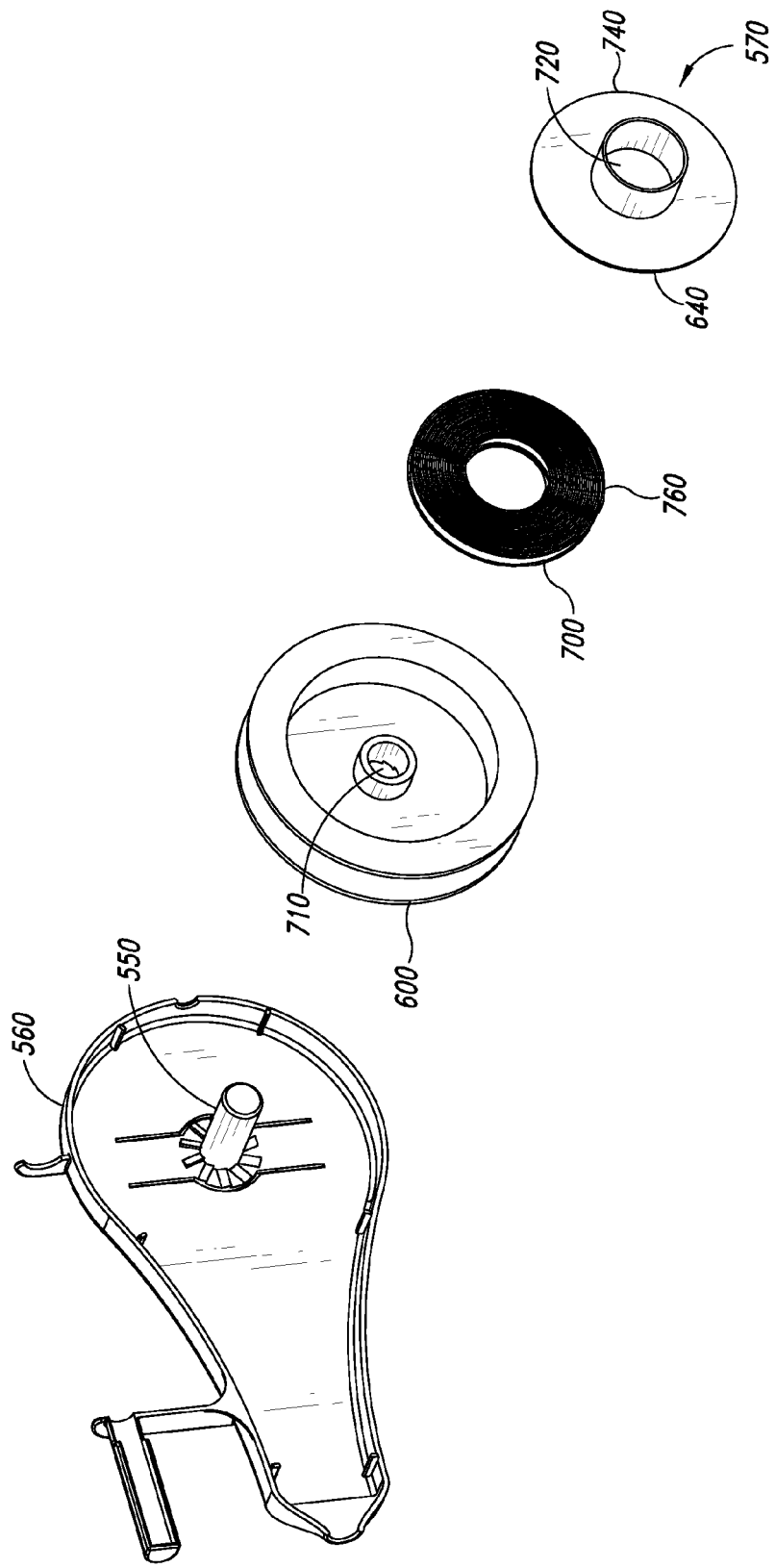
FIG. 9 is an exploded view depicting a cord actuation device mountable to a side housing of the cauterizing system, in accordance with an illustrated embodiment.

FIG. 9 shows the cord actuation device 570, including the control element 550 (illustrated as a rigid rod) projecting outwardly from the housing 560, the spindle assembly 600 (which is shown in this embodiment as a reel), a biasing member 700, and the spindle assembly 640. To assemble the cord actuation device 570, the control element 550 is inserted and passed through an opening 710 of the spindle assembly 600, the biasing member 700, and an opening 720 of the spindle assembly 640. The control element 550 is then passed through a side opening 724 defined by a tubular holder 726 of the side housing 564 (FIG. 8).

Figure 10:
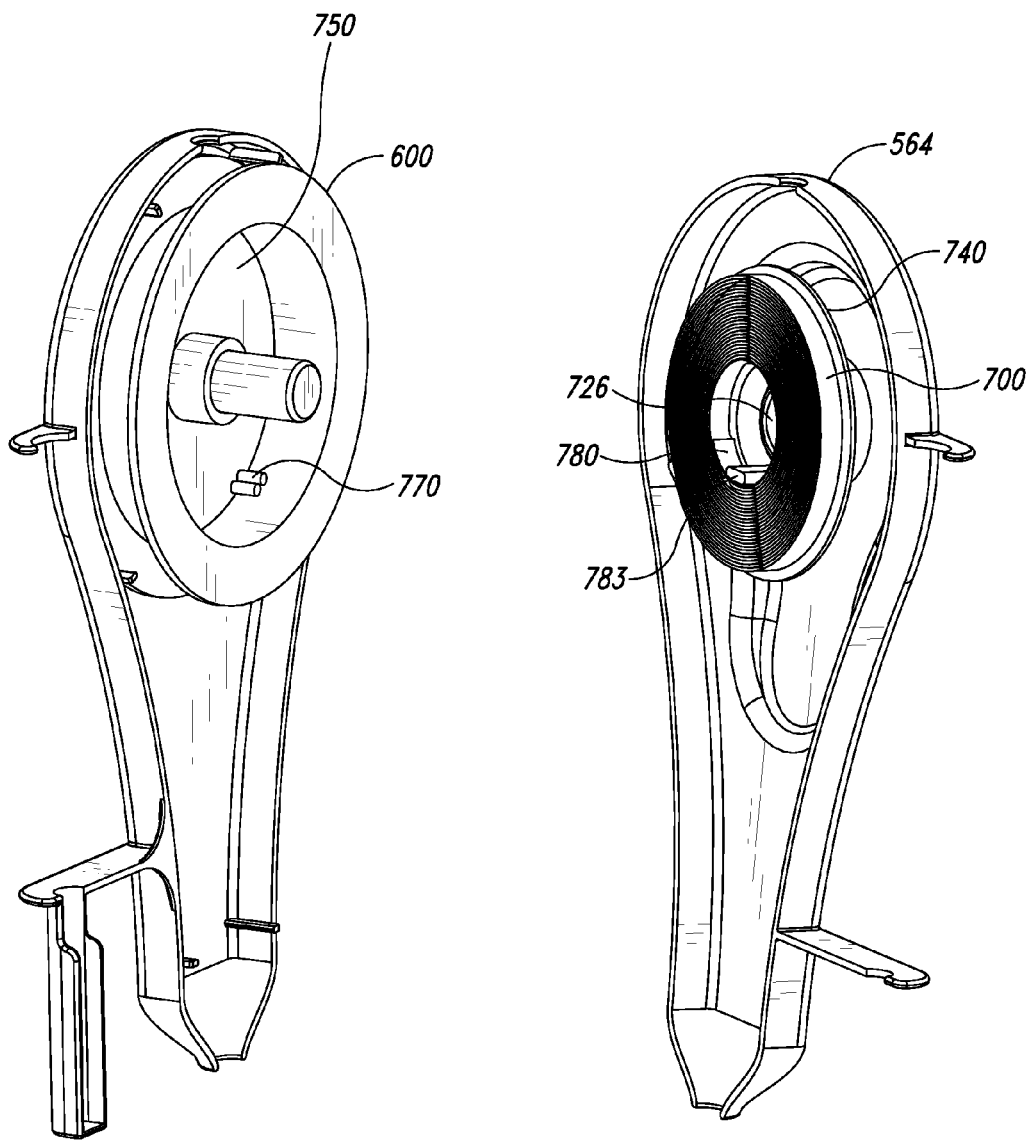
FIG. 10 shows internal components of a cauterizing system.

Referring to FIG. 10, the biasing member 700 can be captured between the spindle assemblies 600, 640 (illustrated disassembled). In some embodiments, including the illustrated embodiment of FIG. 10, the biasing member 700 is sandwiched between a disk shaped plate 740 of the spindle assembly 640 and a face 750 of the spindle assembly 600. An end 760 of the biasing member 700 (FIG. 9) can be coupled to a spring retaining feature 770 of the spindle assembly 600, and another end 780 (FIG. 10) of the biasing member 700 can be coupled to a spring retaining feature 783 of the side housing 564. The spring retaining features can be arms or other types of cantilevered members. Other types of spring mounting arrangements are also possible. The biasing member 700 can be in the form of a coiled spring, helical spring, spiral spring, combinations thereof, or the like to provide the desired biasing forces.

Figure 11:
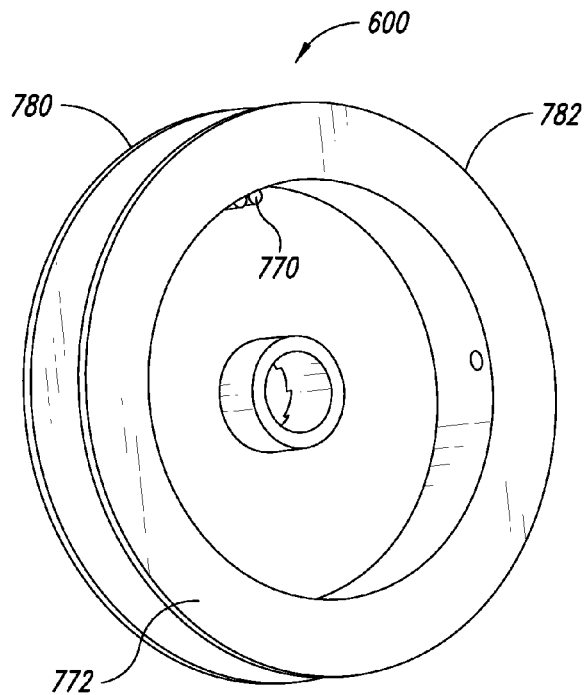
FIGS. 11-13 illustrate a spindle assembly for receiving a cauterizer cord, in accordance with one illustrated embodiment.
Figure 12:
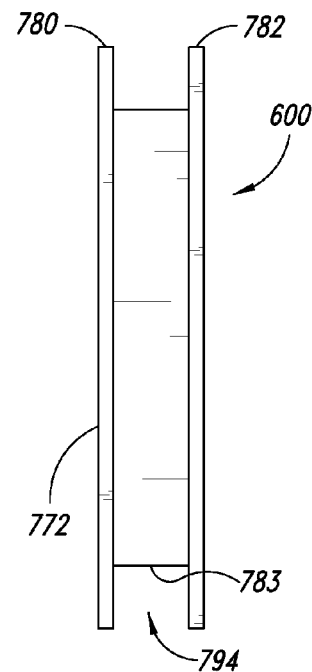
Figure 13:
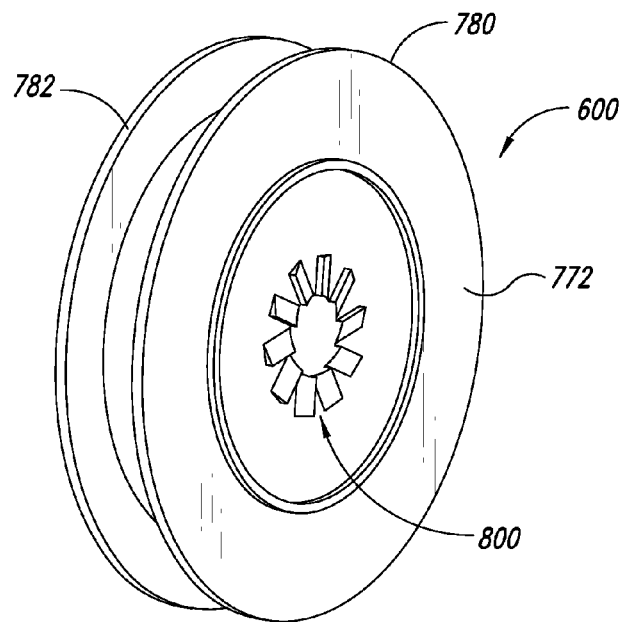

Referring to FIGS. 11-13, the spindle assembly 600 further includes a spindle 772 (illustrated as a reel) including two end plates 780, 782 and a drum 783 that define a channel 794 for receiving the handpiece cord 530. As used herein, the term "reel" is broadly construed to include, without limitation, spools, holders about which cords can be wound, and other types of one-piece or multi-piece cord holding devices.

Figure 14:
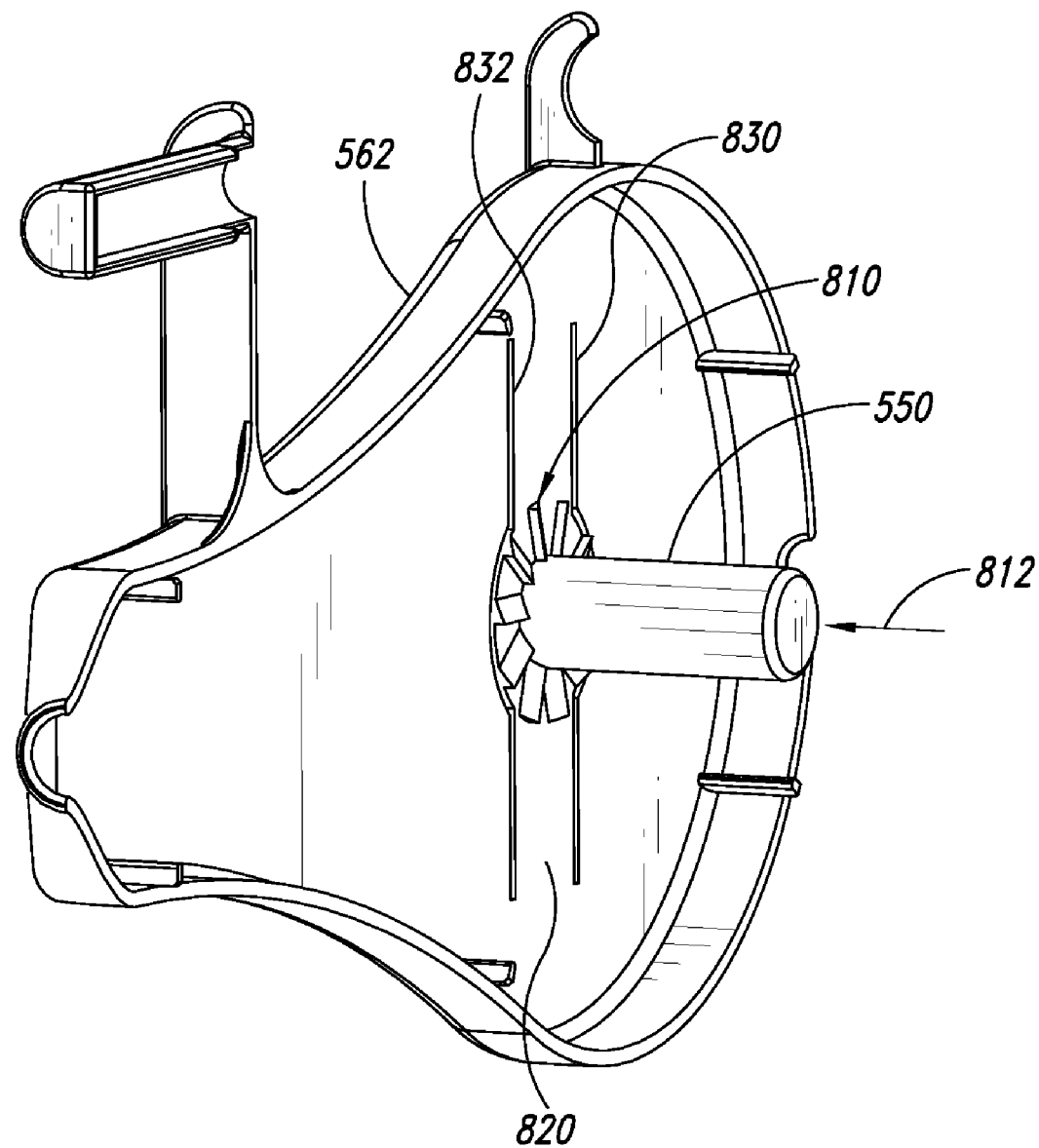
FIG. 14 is an isometric view of a side housing having a control element for operating a cord actuation device, in accordance with one illustrated embodiment.

The spindle assembly 600 can allow for movement in one direction and can arrest movement in the opposite direction. The cord actuation device 570 provides ratcheting movement of the spindle assembly 600 because a plurality of engagement features 800 of the spindle assembly 600 (FIG. 13) can selective mate with complementary engagement features 810 the side housing 562 (FIG. 14). Engagement features can include, without limitation, teeth, grooves, protrusions, gears, or other types of features that can provide the desired movement. The illustrated engagement features 800, 810 are radially extending teeth spaced from one another.

When the control element 550 is in its raised position (FIG. 7), the engagement features 800, 810 mate and allow the reel 772 to rotate in the counter-clockwise direction to unwind the cord 530 in response to a user pulling on the handpiece cord 530 and overcoming the bias provided by the biasing member 700. When the biasing member 700 overcomes the applied pulling force or no force is applied, the engagement features 800, 810 may lock and limit rotation of the reel 772 in the clockwise direction.

The control element 550 can be displaced to move the engagement features 810 away from the engagement features 800, thereby unlocking and allowing the biasing member 700 to rotate the reel 772 in the clockwise direction, thereby retracting the handpiece cord 530. When a user presses on the control element 550 (indicated by the arrow 812 of FIG. 14), a flexible sidewall section 820 of the side housing 562 can bend outwardly away from the reel 772, thereby disengaging the features 800, 810. To reengage the features 800, 810, the user allows the displaced control element 550 to return to its raised starting position.

Various other types of cord actuation devices can also be employed. For example, a cord actuation device can include a pawl and a wheel with inclined teeth for engaging the pawl. The pawl and wheel can cooperate to provide unidirectional movement of the spindle assembly 600 or spindle assembly 640, or both. In some embodiments, the spindle assembly 640 freely rotates about the tubular holder 726 of the side housing 564 (FIG. 8). As such, the spindle assemblies 600, 640 may be independently movable with respect to one another. Various combinations of gears, bearings, pawls, wheels, biasing members, and the like can provide the desired movement of the spindle assemblies 600, 640. The cord actuation devices can also include one or more electrical components that couple together components, such as the handpiece cord 530 and the power cord 590. These electrical components can include conductive biasing members, wires, connectors, bonding pads, or the like.

Figure 15:
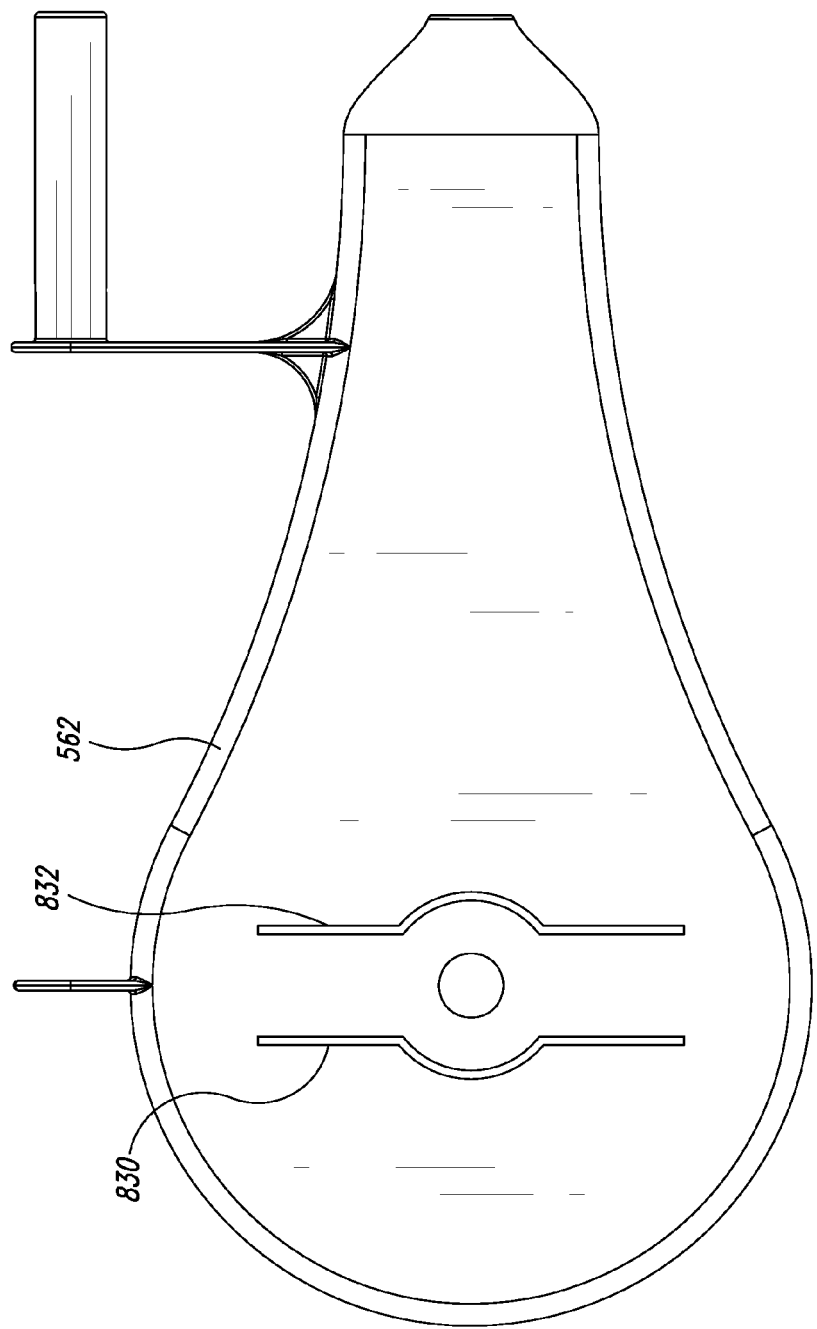
FIG. 15 is a side elevational view of a housing of a cord dispenser, in accordance with one illustrated embodiment.

FIGS. 14 and 15 illustrate the side housing 562 having a pair of cutouts 830, 832 defining the flexible sidewall section 820. The cutouts 830, 832 provide the desired stiffness for actuating the control element 550, illustrated here as interposed between the cutouts 830, 832 and substantially orthogonal to the sidewall section 820. The number and configuration of the cutouts can be selected based on the desired action of the control element 550. Cutouts can be slots, openings, elongated holes, and the like made by machining, a molding process, or other suitable manufacturing process.

Additionally or alternatively, the cutouts 830, 832 can be used to mount the cauterizing system 500 to a mounting structure. In some embodiments, a clip, mounting bracket, arm, or other type of mounting feature can permanently or removably couple the cauterizing system 500 to a mounting stand.

Referring again to FIG. 7, the cord dispenser 510 includes a holder 854 releasably holding the cauterizer handpiece 520. The holder 854 includes a pair of spaced apart retaining members 860, 862 at one end of the cauterizer handpiece 520 and another pair of retaining members 890, 892 at the other end of the cauterizer handpiece 520. To separate the cauterizer handpiece 520 from the cord dispenser 510, a user can comfortably grip and move the handpiece 520 away from the retaining members 860, 862, as indicated by the arrow 865. The handpiece 520 can then be withdrawn from a protective shield 870 that surrounds a cautery tip 880 and pulled away from the retaining members 890, 892. After performing the cauterizing procedure, the user can return the handpiece 520 for convenient storage.

The illustrated retaining members 860, 862, 890, 892 are fixedly coupled to the housing 560 and hold the handpiece 520 proximate to, but spaced from, the housing 560. The number and configuration of the retaining members can be selected based on the configuration of the cauterizer handpiece 520.

The protective shield 870 can help prevent a user from inadvertently striking the cautery tip 880, as well as limiting access to a cautery heating element 881 of the cautery tip 880 so as to reduce the likelihood of accidental burnings while maintaining sterility. In the illustrated embodiment, the protective shield 870 is closed ended and partially surrounds the cautery tip 880. A viewing window 899 provides viewing to determine, for example, whether a desired cautery heating element 881 is installed.

Figure 16:
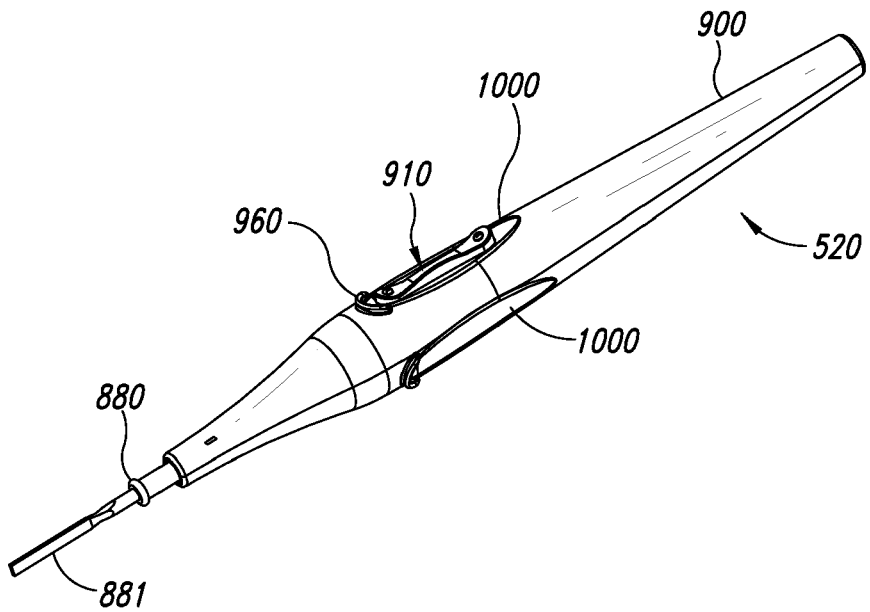
FIGS. 16 and 17 illustrate a cauterizer handpiece, in accordance with one illustrated embodiment.
Figure 17:
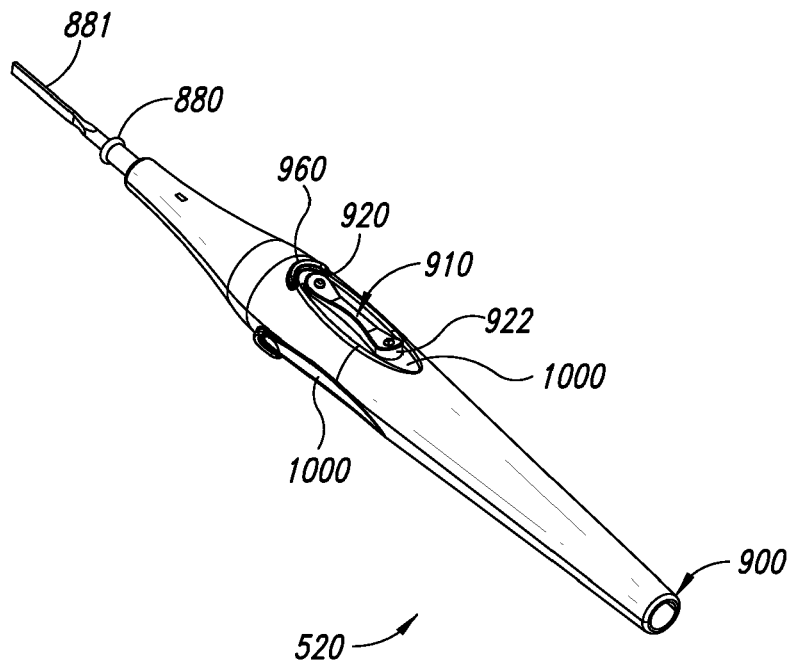

FIGS. 16 and 17 illustrate the cauterizer handpiece 520, including an elongate main body 900 dimensioned and configured to be manually gripped by a user, the cautery tip 880 extending from the elongate main body 900, and a manually operable input device 910 positioned along the elongate main body 900 and spaced from the cautery tip 880.

The input device 910, illustrated as a manually operable rocker button, is used to control the temperature of the heating element 881. The input device 910 of FIG. 17 includes a first contact region 920 and a second contact region 922 space from the first contact region 920. A user can press down on the first and second contact regions 920, 922 to increase or decrease the temperature of the heating element 881. In this manner, a user can accurately control operation of the cautery tip 880.

Additionally or alternatively, the input device 910 can be used by the user to switch the cauterizer handpiece 520 between and ON state for cauterizing tissue and an OFF state. A user, for example, can press on the first and second contact regions 920, 922 to turn the handpiece 520 OFF and ON, respectively.

Referring to FIGS. 18A and 18B, the input device 910 includes traction elements 940, 942 for increased frictional interaction. As used herein, the term "traction element" is broadly construed to include, without limitation, one or more protuberances, grooves, bumps, textured surfaces (e.g., roughened surfaces), and combinations thereof. The illustrated traction elements 940, 942 are protuberances that project outwardly from the first and second contact regions 920, 922, respectively. The traction elements 940, 942 can also be at other locations, if needed or desired. To ensure proper hand positioning, the user can contact use the traction elements 940, 942 for tactile feedback. Thus the elements 940, 942 serve as positioning indicators.

As shown in FIGS. 16-18B, the handpiece 520 includes at least one locator 960 adjacent the input device 910 for positioning at least a portion of a user's hand. The locator 960 can be a stop that extends outwardly from the main body 900 a sufficient distance to stop or limit the amount of sliding of the user's thumb or finger along the handpiece 520. For enhanced control, the distance between the input device 910 and the locator 960 is less than a distance between a free end of the cauterizing element 881 and the locator 960. The position of the locator 960 can be selected based on the shape and axial length of the handpiece 520.

The illustrated locator 960 is an arcuate member surrounding a distal section 970 of the input device 910, as shown in FIG. 18B. If a user's thumb inadvertently slides off of the input device 910, the thumb can contact and rest against the locator 560, thereby preventing the thumb from sliding distally towards the heated cautery tip 880. Accordingly, the locator 960 may function as a guard and may reduce the likelihood of an accidental user burnings.

The elongate main body 900 includes a plurality of contoured sections 1000 for accommodating portions of a user's hand when the user operates the cauterizer handpiece 520. The illustrated contoured sections 1000 are circumferentially spaced from one another and positioned medially along the main body 900. Locators 960 are positioned distally of respective contoured sections 1000. Each of the countered sections 1000 is a smooth concave surface (e.g., a depression) having a generally elliptical shape, as viewed from the side. Other configurations are also possible. For example, the contoured sections 1000 can be circular depressions in the main body 900.

Figure 19:
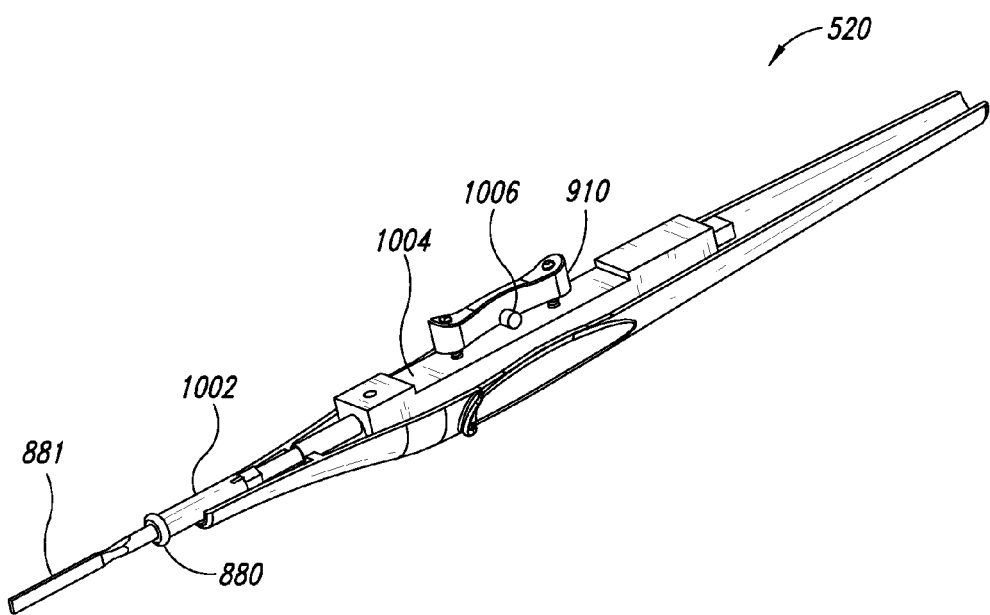
FIG. 19 shows internal components of a cauterizer handpiece, in accordance with one illustrated embodiment.

FIG. 19 illustrates internal components of the cauterizer handpiece 520. The cautery tip 880 includes the heating element 881 and an adapter assembly 1002 holding the heating element 881. An interconnect 1004 engages the input device 910 and the adapter assembly 1002. The input device 910 includes rods 1006 for pivotally coupling the input device 910 to the main body 900 (shown partially removed).

Figure 20:
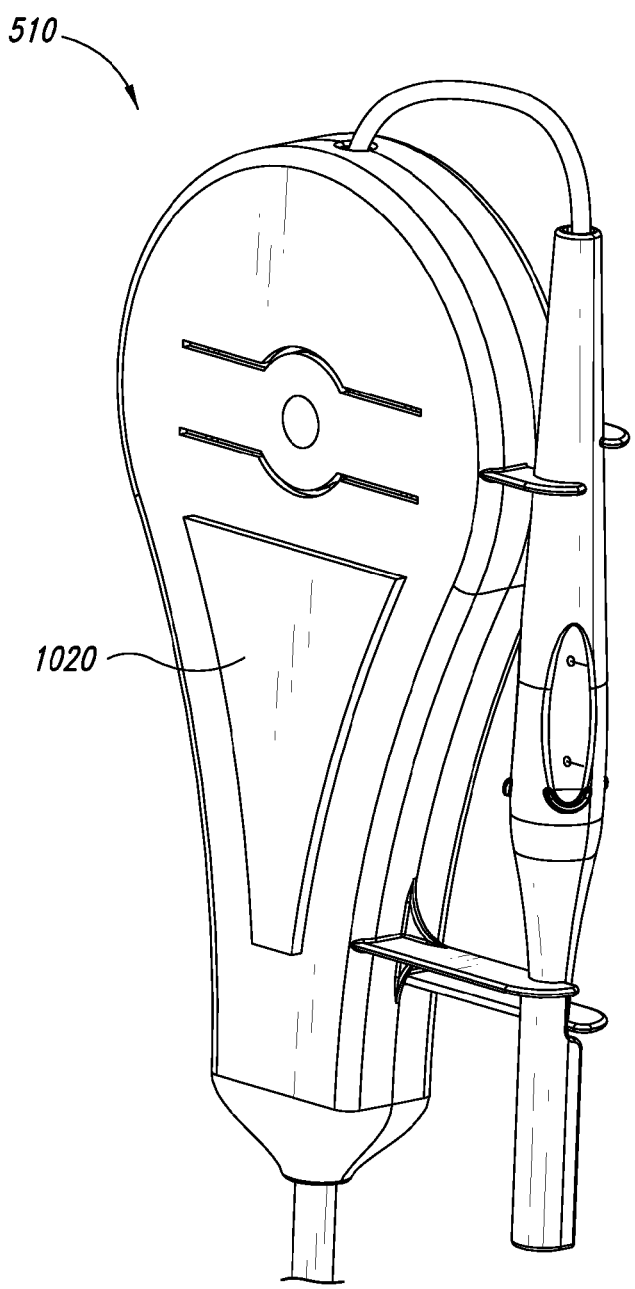
FIG. 20 is an isometric view of a cauterizing system having a mounting system, in accordance with one illustrated embodiment.
Figure 21:
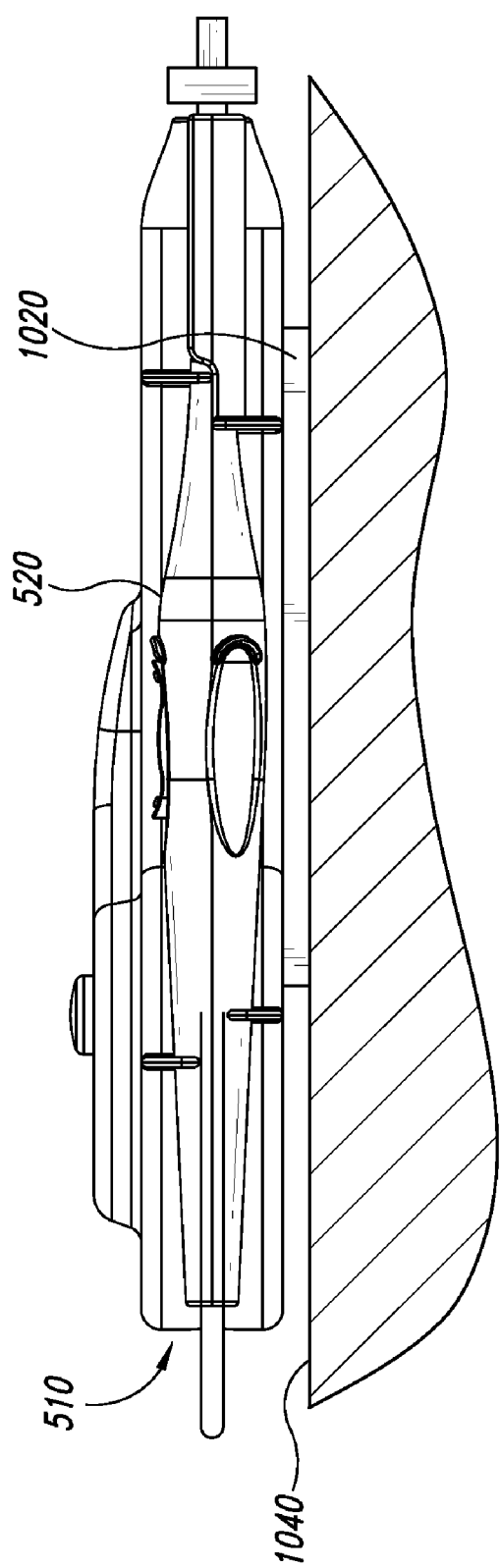
FIG. 21 illustrates the cauterizing system of FIG. 20 coupled to surface via the mounting system.

The cauterizing system of FIG. 7 can include a mounting system for mounting to a surface. For example, FIG. 20 illustrates a mounting system 1020 that may be similar to the mounting system 300 of FIGS. 5 and 6 discussed above. As shown in FIG. 21, the mounting system 1020 couples the cord dispenser 510 to a surface 1040 such that a user can conveniently access and use the handpiece 520. The mounting system 1020 remains securely anchored to the surface 1040 and the cauterizer handpiece 520 is used.

Figure 22:
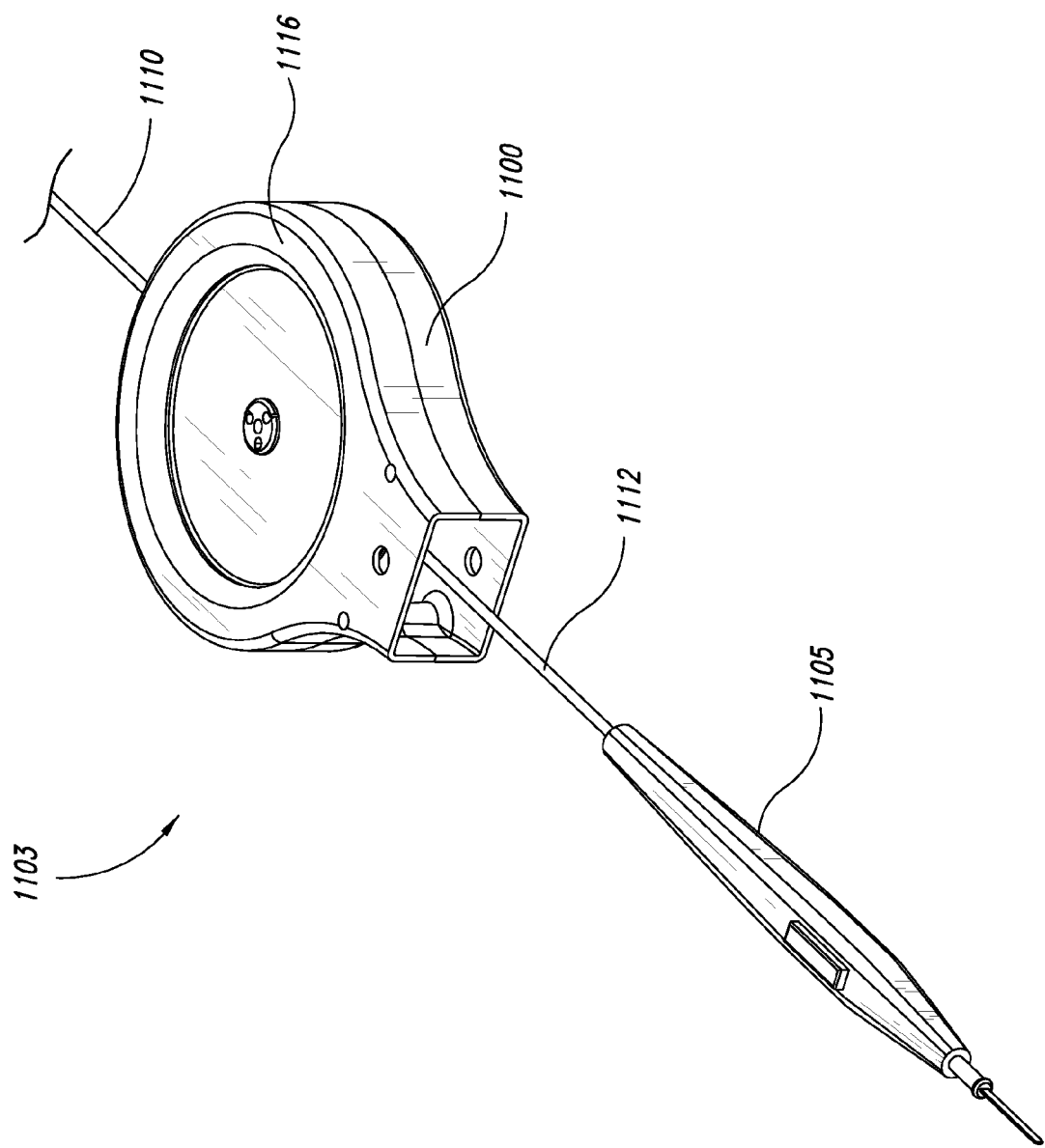
FIG. 22 is a frontal isometric view from the top left side of cauterizing system formed in accordance with another embodiment of the present disclosure.

FIG. 22 shows a system 1103 that includes a cord dispenser 1100 and an instrument 1105. The cord dispenser 1100 includes an internal cord actuation device 1107 (FIG. 23) with a conductive biasing member 1108 and a spindle assembly 1113 that is physically coupled to the biasing member 1108. The biasing member 1108 electrically couples a cord 1110 to an instrument cord 1112. The instrument cord 1112 can be repeatedly wound onto and unwound from the spindle assembly 1113, while the cord actuation device 1107 continuously provides power from the cord 1110 to the cord 1112. The instrument 1105 can be operated without any appreciable changes in current profiles for consistent operation.

Figure 23:
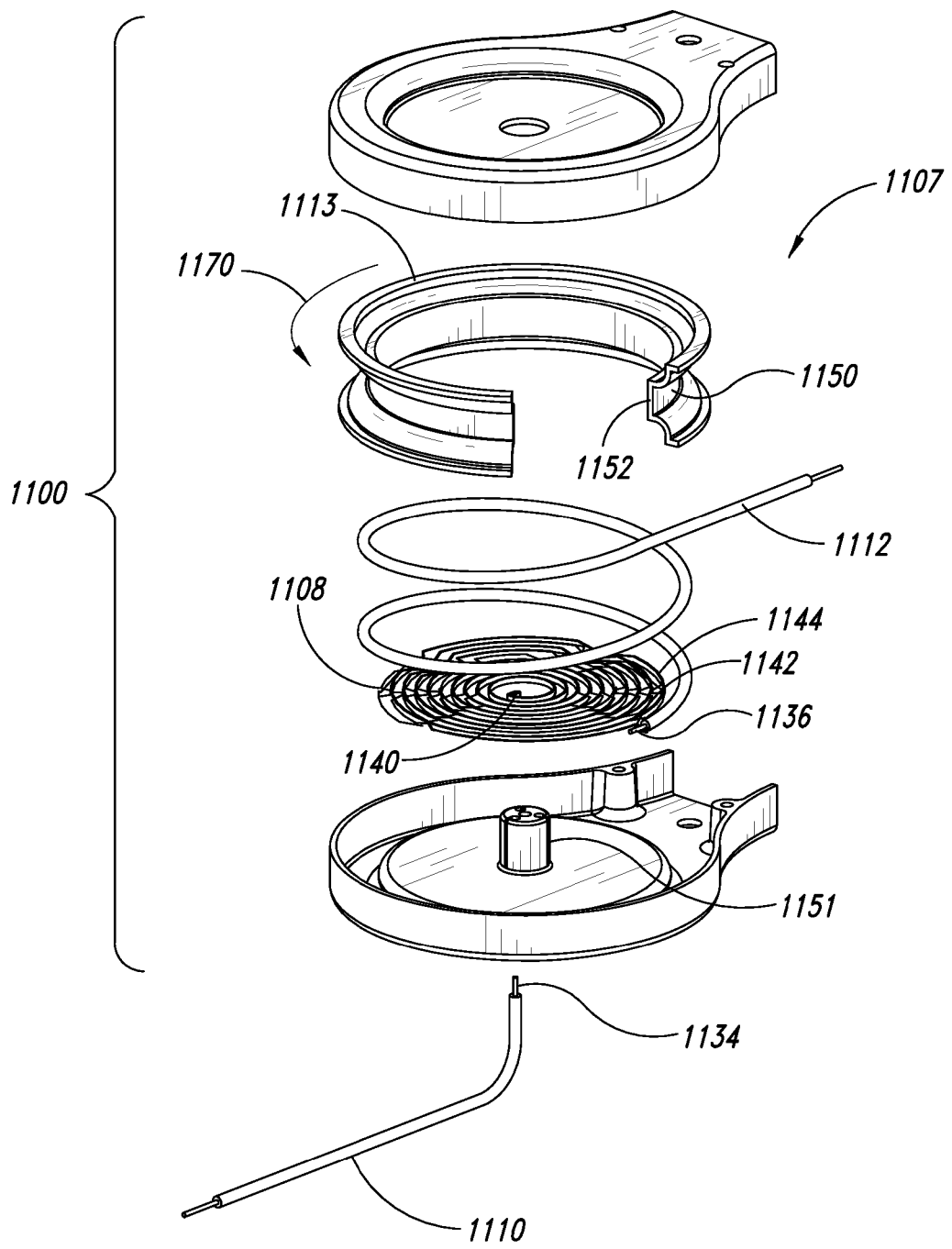
FIG. 23 is an exploded view of a portion of the system of FIG. 22.

The biasing member 1108 of FIG. 23 can conduct electrical current or transmit signals (e.g., control signals, data, waveforms, or the like), or both. The biasing member 1108 also biases the spindle assembly 1113 to allow the instrument cord 1112 to be pulled from a housing 1116 and to actively retract the cord 1112 into the housing 1116 without disrupting communication between the cords 1110, 1112.

The cord 1110 can include a plug. An end 1134 of the cord 1110 is electrically coupled to an inner end 1140 of the biasing member 1108. The cord end 1134 and the inner end 1140 can join together within or proximate to a post 1151. An end 1136 of the cord 1112 is coupled to an outer end 1142 of the biasing member 1108. Connectors, solder, or other types of electrical components can directly or indirectly couple the cords 1110, 1112 to the biasing member 1108. The biasing member 1108 is positioned between the post 1151 and the spindle assembly 1113. The post 1151 is fixedly coupled to the housing 1116, such that the cord end 1134 and the inner end 1140 of the biasing member 1108 are generally stationary as the spindle assembly 1113 rotates.

A main body 1144 of the biasing member 1108 extends in a circular fashion between the ends 1140, 1142. In some embodiments, including the illustrated embodiment of FIG. 23, the biasing member 1108 is a spiral spring that may include, without limitation, one or more resilient members (including stiffeners), conductors, insulators, coverings, or the like. Resilient members can provide a biasing force and can be made of spring steel or other suitable material. Resilient members can also provide both a biasing force and electrical communication. Conductors can be wires or traces made of a highly conductive material, such as copper or aluminum. In some embodiments, the biasing member 1108 includes a resilient member and a conductor that is bonded to the resilient member. Coverings can be made of an insulating material. For example, a covering can surround and protect a resilient member and a conductor. In other embodiments, the biasing member 1108 is a unitary structure made of a resilient and electrically conductive material that both conducts electricity and provides a biasing force. The configuration, material composition, and components, if any, of the biasing member 1108 can be selected based on the desired mechanical and electrical properties.

The spindle assembly 1113 defines a channel 1150 in which the cord 1112 is wound. An opening 1152 in the spindle assembly 1113 provides access to the biasing member 1108. The cord 1112 and the biasing member 1108 form a junction that can be fixedly coupled to the spindle assembly 1113 at least proximate to the opening 1152. Welding, couplers, adhesives, fasteners, or combinations thereof can be used to couple at least one of the cord 1112 and biasing member 1108 to the spindle assembly 1113. The illustrated opening 1152 of FIG. 23 is a gap in a discontinuous spool. In other embodiments, the opening 1152 is a through-hole in a continuous spool. A wide range of different types of openings can provide access through spindle assemblies.

The spindle assembly 1113 is rotatably coupled to the housing 1116 by one or more bearings (e.g., ball bearing assemblies, roller bearing assemblies, or the like). The biasing member 1108, the spindle assembly 1113, and the post 1151 lie generally along a single plane and are positioned at a central location of the cord dispenser 1100, such that the system 1103 has a relatively small thickness.

The cord 1112 can be pulled to rotate the spool assembly 1113, as indicated by the arrow 1170 in FIG. 23, to extend the cord 1112. As the spool assembly 1113 rotates, the biasing member 1108 is tightened and provides a biasing force to retract the cord 1112. When a user releases the instrument 1105, the cord 1112 is retracted into the housing 1116. A control element can be incorporated into the system 1103 to selectively lock and unlock the spindle assembly 1113, if needed or desired. The control elements can be operated manually, automatically, or both. A sterile environment can be maintained in the housing 1116, even though the outside environment surrounding the housing 1116 may be non-sterile. Cross-contamination between the cords 1112, 1132 can thus be minimized, limited, or substantially eliminated.

The system 1103 of FIG. 23 can have multiple spindle assemblies. For example, the system 1103 can have an additional spindle assembly capable of independently retracting another cord. The number, orientation, and position of the spindle assemblies can be selected based on the desired functionality of the system 1103.

Figure 24:
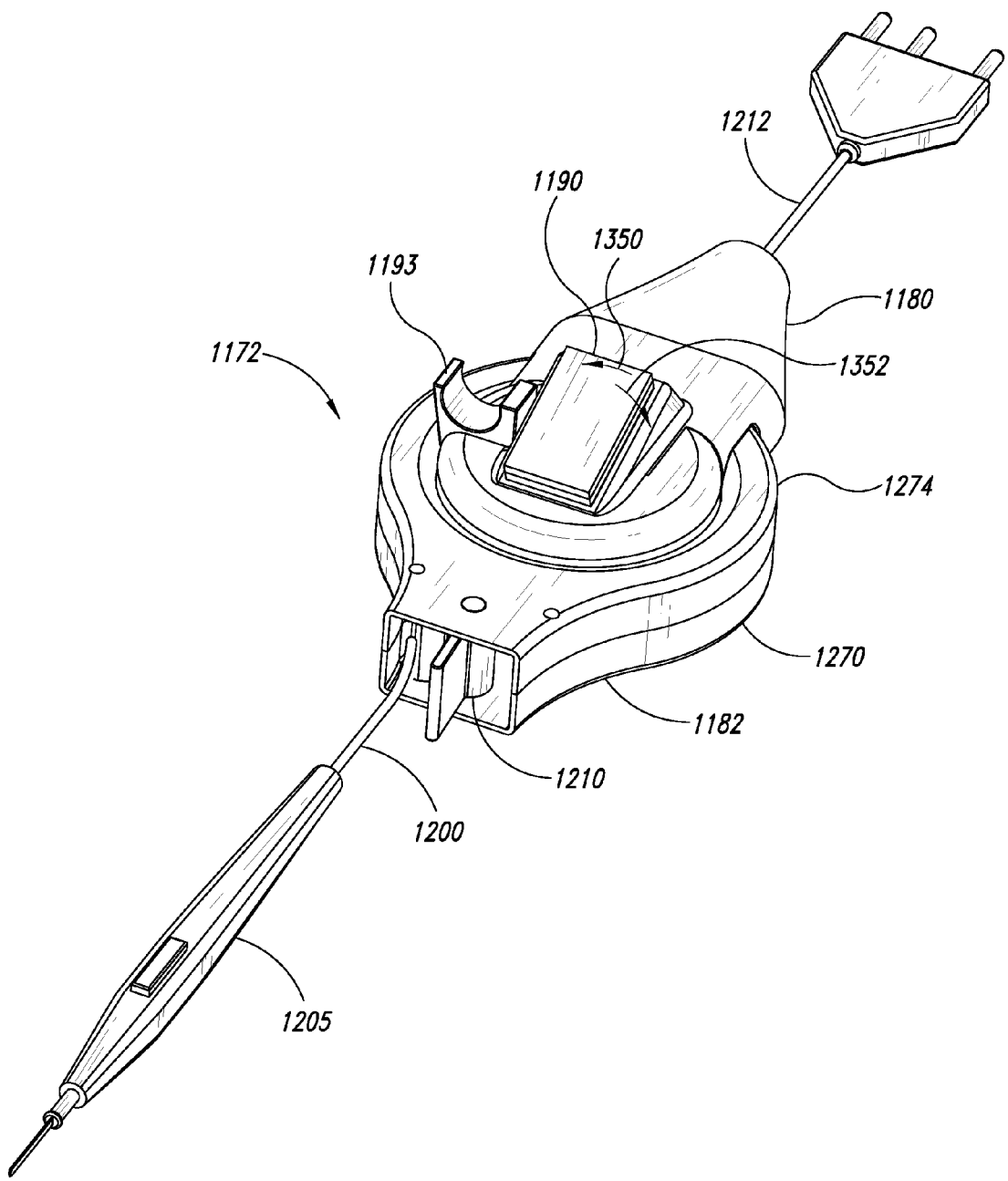
FIG. 24 is a frontal isometric view from the top left side of cauterizing system formed in accordance with another embodiment of the present disclosure.
Figure 25:
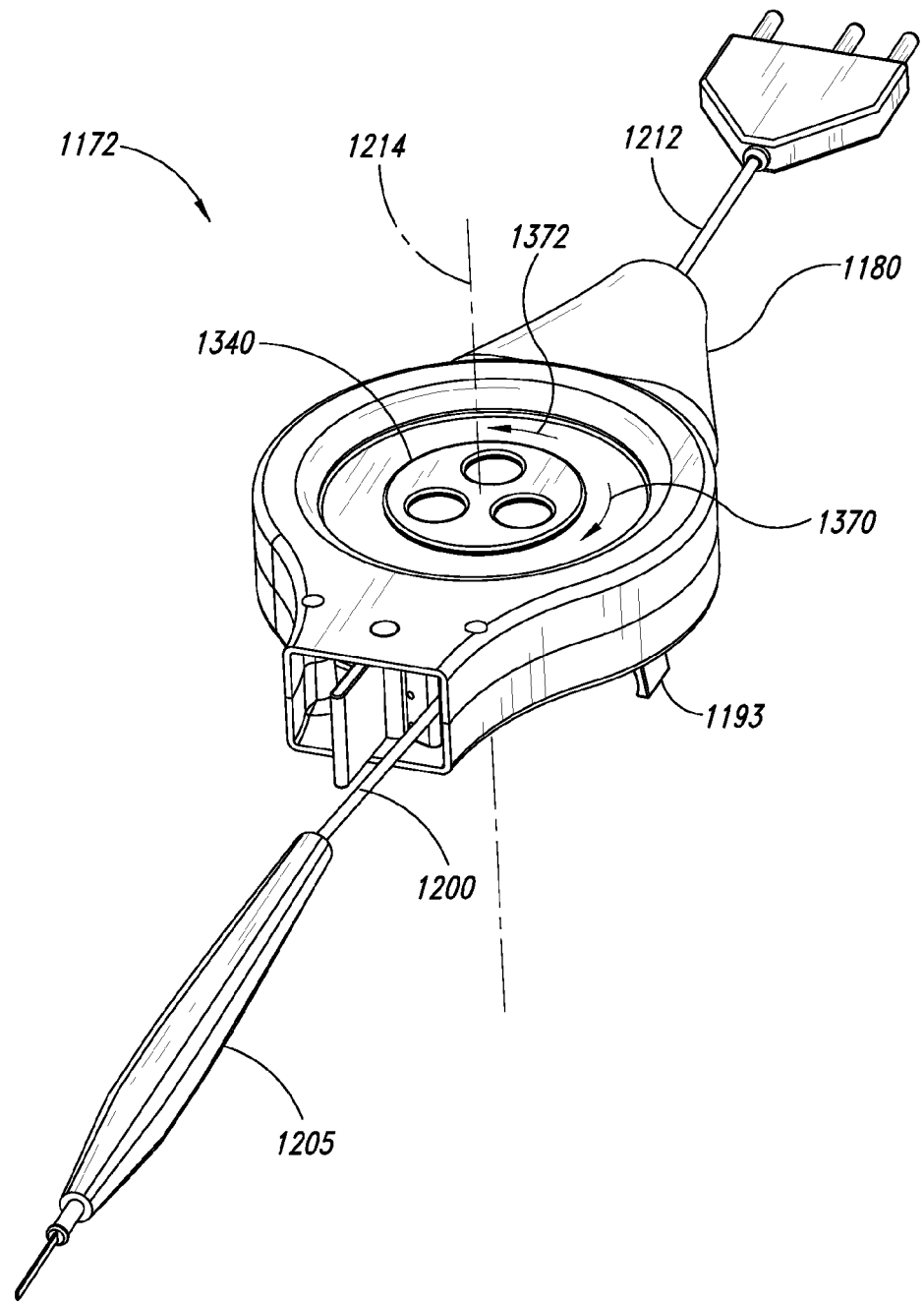
FIG. 25 is a isometric view from the bottom of the cauterizing system of FIG. 24.

FIGS. 24 and 25 show a system 1172 including a main body 1182 and a cord guide 1180 movable with respect to the main body 1182. A scratch pad 1190 is movably coupled to the cord guide 1180. An instrument holder 1193 is positioned adjacent to the scratch pad 1190. A power cord 1212 extends from the cord guide 1180, and a cord 1200 extends from the main body 1182. A cord locking mechanism 1210 is operable to selectively hold the cord 1200.

Figure 26:
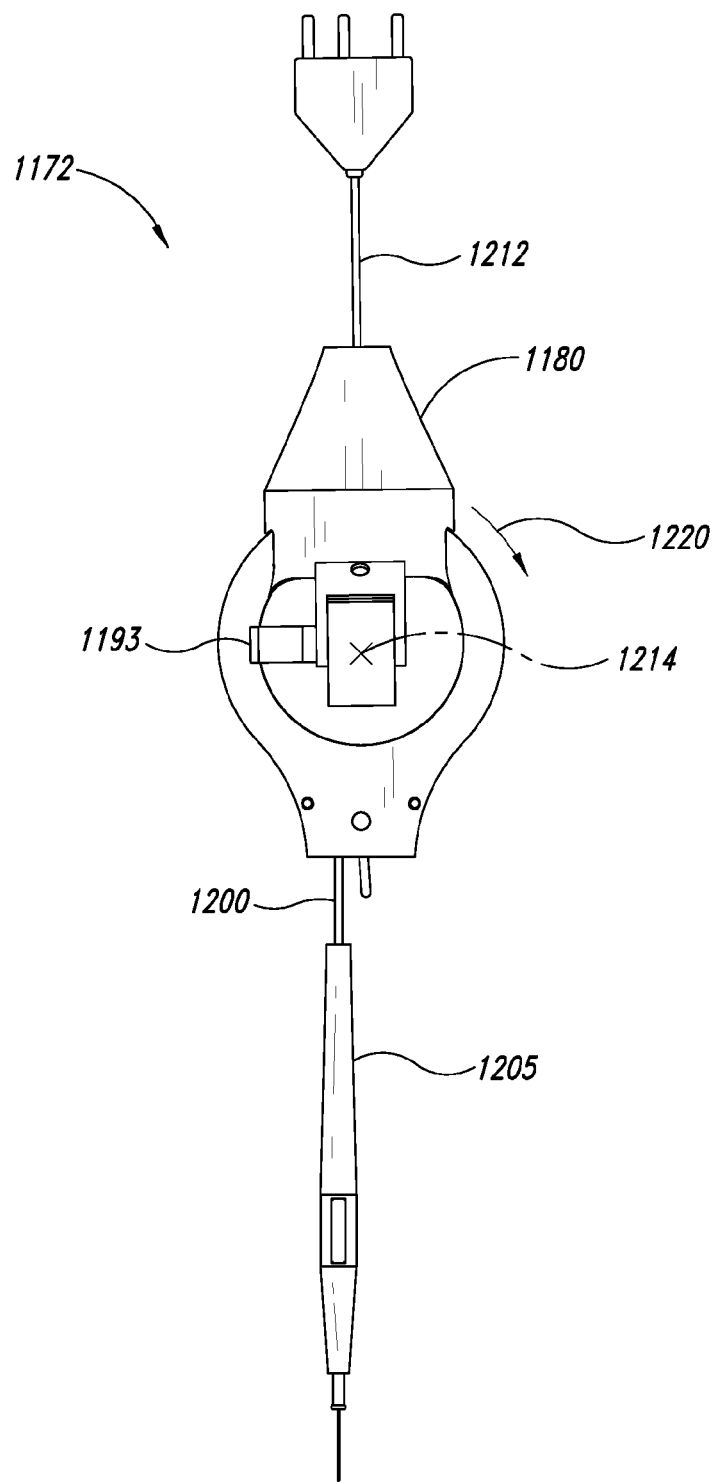
FIGS. 26 and 27 are plan views of the system of FIG. 24 in different configurations.
Figure 27:
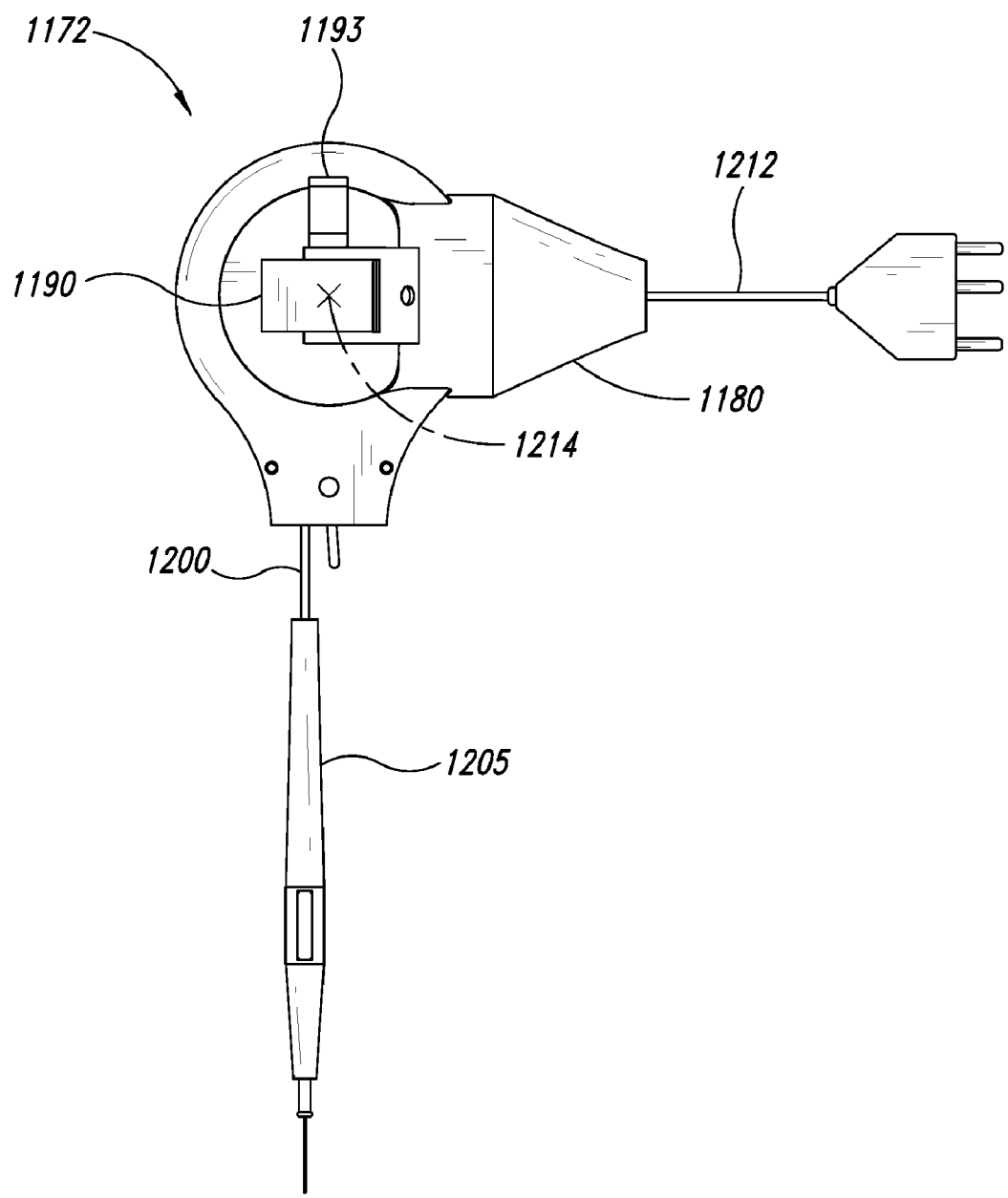

Referring to FIGS. 26 and 27, the cord guide 1180 can have a hollow configuration and a generally frusto-conical shape. The cord guide 1180 rotates about an axis of rotation 1214 to change the relative positions of the cords 1212, 1200. For example, the cord guide 1180 can be rotated clockwise, as indicated by the arrow 1220 in FIG. 26, about the axis of rotation 1214 to another position, as shown in FIG. 27. The cord guide 1180 can be swiveled to direct the cords 1200, 1212 in the general direction of a patient and a power source, respectively. The system 1172 can be moved to different configurations without any appreciable changes in electrical profile (e.g., frequency, voltage, and/or amperage). In some embodiments, an instrument 1205 is a cauterizer that can be maintained at a desired temperature without any disruption of power when the system 1172 is repeatedly reconfigured.

Figure 28:
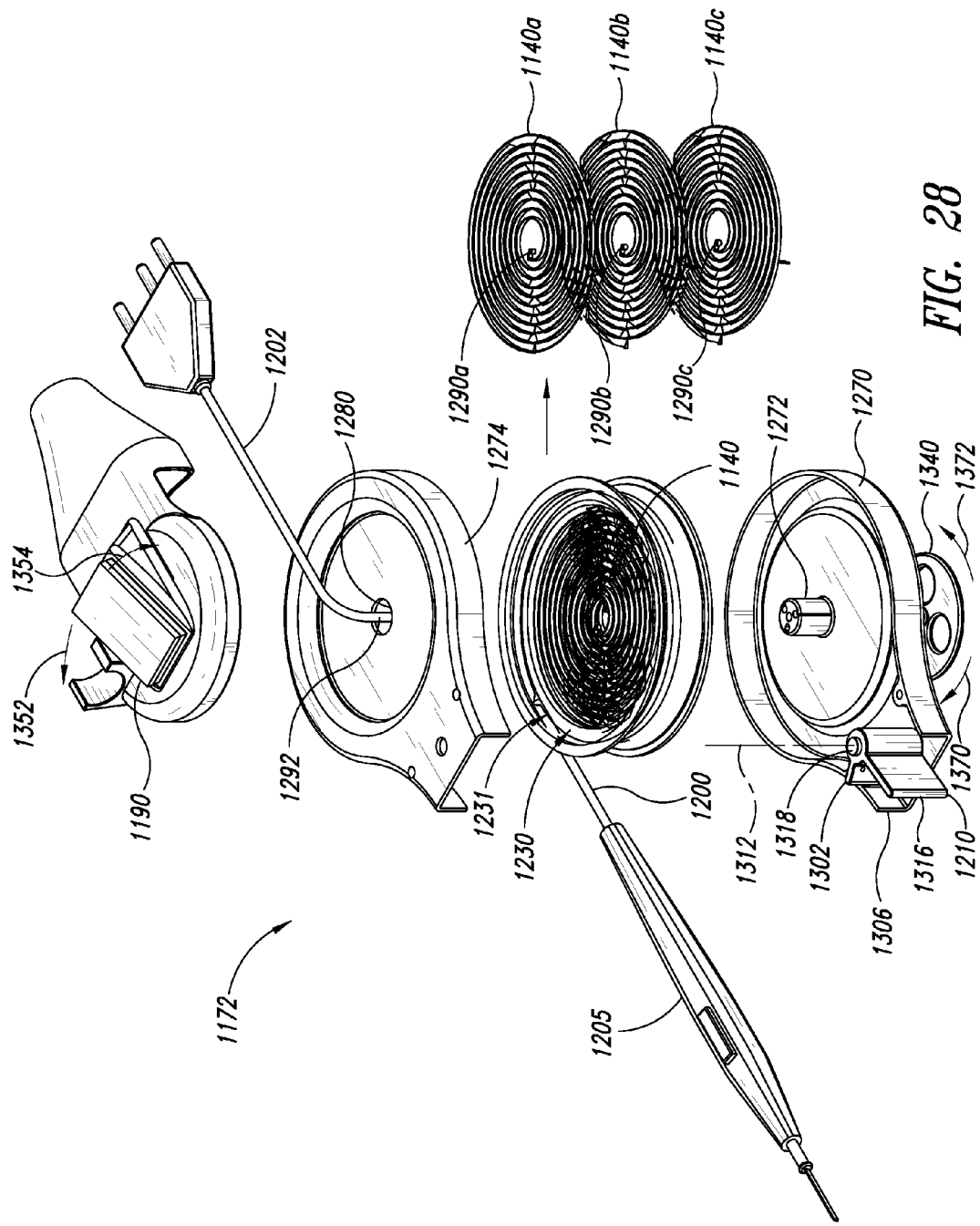
FIG. 28 is an exploded view of the system of FIG. 24.

Referring to FIG. 28, a cord actuation device 1230 includes a plurality of biasing members 1240a, 1240b, 1240c (collectively 1240) for providing electrical power to the three-wire power cord 1200. Each biasing member 1240 can provide electrical communication between a wire in the cord 1200 and the power cord 1202. Independent circuits can be maintained in this manner.

Referring to FIGS. 24 and 28, the housing 1182 includes a side housing 1270 with a post 1272 and a side housing 1274 with an opening 1280. When the side housings 1270, 1274 are coupled together, the post 1272 extends through the opening 1280. The side housings 1272, 1274 define an enclosure for maintaining a sterile environment within the housing 1182 while providing access to internal electrical components.

The inner ends 1290a, 1290b, 1290c (collectively 1290) can be coupled to the post 1272. An end 1292 of the cord 1200 can be coupled to the post 1272 and electrically coupled to the inner ends 1290.

The biasing members 1140 can be covered with an insulator to insulate the members 1140 from one another. Alternatively, biasing members 1140 can be interleaved with insulating disks or other types of insulators. The stack of biasing members 1140 thus provides independent circuits for powering instruments.

The locking mechanism 1210 can be operated to selectively restrain and release the cord 1200. The illustrated locking mechanism 1210 in FIG. 28 is in a locked position to capture the cord 1200 between an arm 1302 and a sidewall 1306 of the side housing 1270. The locking mechanism 1210 is rotatable (e.g., manually rotatable, automatically rotatable, or both) about an axis of rotation 1312 by moving an outwardly extending lever 1316. The mechanism 1210 can be rotated to move the arm 1302 away from the sidewall 1306. A shaft 1318 is fixedly coupled to the side housing 1270 and defines the axis of rotation 1312. A wide range of different types of locking mechanisms can be used to prevent movement of the cord 1200. Actuators, springs, or the like can be incorporated into the locking mechanism 1210. Of course, another locking mechanism can be carried by the strap guide 1180 if the cord 1202 is also retractable. By way of example, a locking mechanism can be within or proximate the opening of the cord guide 1180.

The cord 1200 can be pulled from the spindle assembly 1231 while the locking mechanism 1210 is in an unlocked position. The biasing members 1140 are tightened as the spool assembly 1231 rotates. After a desired length of the cord 1200 has been dispensed, the locking mechanism 1210 is moved to the locked position. To recoil the cord 1200, the locking mechanism 1210 is moved to the unlock position to allow the biasing members 1140 to rotate the spool assembly 1231.

An actuator 1340 can be rotated to move the scratch pad 1190 outwardly (as indicated by the arrow 1352) and inwardly (as indicated by the arrow 1354). For example, the actuator 1340 can have a pin that pushes the scratch pad 1190 outwardly as the actuator 1340 is rotated clockwise (indicated by the arrow 1370 in FIG. 28) and that pulls the pad 1190 downwardly as the actuator 1340 rotates counterclockwise (indicated by the arrow 1372). Additionally or alternatively, the actuator 1340 can adjust the operation of internal components and/or the amount of force required to rotate the spindle assembly 1230. In some embodiments, the actuator 1340 is a thumbscrew capable of rotatably fixing the cord guide 1280 with respect to the housing 1182. The actuator 1304 can selectively unlock the cord guide 1280.

The scratch pad 1190 can have a roughen surface for cleaning instruments. The location and dimensions of the scratch pad 1190 can be selected based on the configuration of the instrument 1105. Other types of components used with the instrument 1105 can also be incorporated into or coupled to the system 1172.

The articles disclosed herein may be formed through any suitable means. For example, the housing of the cauterizing system can be formed through one or more machining processes, molding processes, stamping processes, combinations thereof, and the like. The various methods and techniques described above provide a number of ways to carry out the illustrative embodiments. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. A cauterizing system, for example, can have multiple mounting systems, such as a hook and loop fastener and an angled arm. Mounting systems can be incorporated into the apparatuses disclosed herein. For example, mounting systems can be coupled to the cauterizing systems discussed in connection with FIGS. 22-28. Similarly, the various features and steps discussed above, as well as other known equivalents for each such feature or step, can be mixed and matched by one of ordinary skill in the art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof.

What is claimed is:

1. A cord refractor device, comprising
   a housing;
   a power cord;
   an instrument cord; and
   a resilient conductor in the housing, the resilient conductor is a spring electrically connected to the power cord and the instrument cord to receive power from the power cord and deliver power to the instrument cord and to allow the instrument cord to extend from the housing in response to pulling the instrument cord and to retract the instrument cord into the housing.

2. The cord retractor device of claim 1, wherein the resilient conductor is a spiral spring having a first end and a second end, the first end is coupled to the power cord, and the second end is coupled to the instrument cord.

3. The cord retractor device of claim 1, further comprising a strap guide movable with respect to the housing, one of the instrument cord and the power cord extends through and out of the strap guide.

4. The cord retractor device of claim 1, wherein the resilient conductor is a spiral spring and the cord retractor device comprises a spool surrounding the spiral spring, the spring structured to bias the spool to retract the instrument cord into the housing and to wind the instrument cord about the spool.

5. The cord retractor device of claim 1, wherein the resilient conductor includes a plurality of electrically conductive biasing members electrically insulated from one another, each biasing member electrically coupling respective wires in the instrument cord to respective wires in the power cord.

6. The cord retractor device of claim 1, further comprising a locking mechanism carried by the housing, the locking mechanism movable between a first configuration to retain the instrument cord and a second configuration to release the instrument cord.

7. The cord retractor device of claim 1, further comprising a scratch pad coupled to the housing.

8. The cord retractor device of claim 7, wherein the scratch pad is movable between a first position and a second position.

9. A device, comprising:
   a power cord structured to conduct current;
   an instrument cord structured to conduct current; and
   an electrical conductor that is a spring electrically coupled to the power cord and the instrument cord to receive power from the power cord and to deliver power to the instrument cord and to allow the instrument cord to extend away from the power cord in response to pulling the instrument cord and to retract the instrument cord towards the power cord.

10. The device of claim 9, wherein the electrical conductor comprises a spiral spring having a first end and a second end, the first end electrically coupled to the power cord and the second end electrically coupled to the instrument cord.

11. The device of claim 9, wherein the electrical conductor comprises a spiral spring and a spool surrounding the spiral spring, the spiral spring structured to bias the spool to retract the instrument cord towards the power cord and to wind the instrument cord around the spool.

12. The device of claim 9, wherein the power cord comprises a plurality of conducting wires, and the instrument cord comprises a plurality of conducting wires, and the cord actuation device comprises a plurality of electrical conductors structured as spring members that are each electrically coupled to a respective one of the conducting wires in the power cord and the conducting wires in the instrument cord and structured to conduct electrical current from the respective conducting wire in the power cord to the conducting wire in the instrument cord and to allow the conducting wires in the instrument cord to extend away from the conducting wires in the power cord in response to pulling of the instrument cord and to retract the instrument cord towards the power cord when the instrument cord is released.

13. The device of claim 9, wherein the cord actuation device comprises a first cord actuator electrically coupled to the power cord and to a connector cord, and a second cord actuator electrically coupled to the instrument cord and to the connector cord, the first cord actuator structured to allow the power cord to extend away from the connector cord in response to pulling the power cord and to retract the power cord towards the connector cord, and the second cord actuator structured to allow the instrument cord to extend away from the connector cord in response to pulling the instrument cord and to retract toward the connector cord.

14. The device of claim 13, wherein the first cord actuator comprises an electrical conductor in the form of a spiral spring having a first end electrically coupled to the power cord and the second end electrically coupled to the connector cord to conduct power between the power cord and the connector cord, and the second cord actuator comprising an electrical conductor in the form of a spiral spring having a first end electrically coupled to the instrument cord and the second end electrically coupled to the connector cord to conduct power between the connector cord and the instrument cord.

* * * * *